(12) United States Patent
Steemers et al.

(10) Patent No.: US 11,760,772 B2
(45) Date of Patent: Sep. 19, 2023

(54) FUNCTIONALIZATION AND PURIFICATION OF MOLECULES BY REVERSIBLE GROUP EXCHANGE

(71) Applicant: Illumina, Inc., San Diego, CA (US)

(72) Inventors: Frank J. Steemers, Encinitas, CA (US); Kevin L. Gunderson, Encinitas, CA (US); Kerri York, Elizabeth, CO (US); Ryan Christopher Smith, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 115 days.

(21) Appl. No.: 17/330,853

(22) Filed: May 26, 2021

(65) Prior Publication Data

US 2021/0277043 A1   Sep. 9, 2021

Related U.S. Application Data

(63) Continuation of application No. 16/414,593, filed on May 16, 2019, now Pat. No. 11,021,504, which is a continuation of application No. 15/431,470, filed on Feb. 13, 2017, now Pat. No. 10,294,258, which is a continuation of application No. 14/717,312, filed on May 20, 2015, now Pat. No. 9,598,453, which is a continuation of application No. 13/565,400, filed on Aug. 2, 2012, now Pat. No. 9,040,678.

(60) Provisional application No. 61/515,663, filed on Aug. 5, 2011.

(51) Int. Cl.
| | |
|---|---|
| C07H 1/06 | (2006.01) |
| C12Q 1/6811 | (2018.01) |
| C07H 21/00 | (2006.01) |
| C12N 15/10 | (2006.01) |
| C07D 495/04 | (2006.01) |
| C07H 1/00 | (2006.01) |

(52) U.S. Cl.
CPC ............. *C07H 1/06* (2013.01); *C07D 495/04* (2013.01); *C07H 21/00* (2013.01); *C12N 15/1003* (2013.01); *C12Q 1/6811* (2013.01); *C07H 1/00* (2013.01)

(58) Field of Classification Search
None
See application file for complete search history.

(56) References Cited

U.S. PATENT DOCUMENTS

| | | | |
|---|---|---|---|
| 4,868,105 A | 9/1989 | Urdea et al. | |
| 5,034,506 A | 7/1991 | Summerton et al. | |
| 5,432,272 A | 7/1995 | Benner | |
| 5,900,481 A | 5/1999 | Lough et al. | |
| 6,544,732 B1 | 4/2003 | Chee et al. | |
| 6,737,236 B1 | 5/2004 | Pieken et al. | |
| 7,375,234 B2 | 5/2008 | Sharpless et al. | |
| 7,427,678 B2 | 9/2008 | Pieken et al. | |
| 7,763,736 B2 | 7/2010 | Sharpless et al. | |
| 9,040,678 B2 | 5/2015 | Steemers et al. | |
| 9,598,435 B2 | 3/2017 | Steemers et al. | |
| 2012/0258870 A1 | 10/2012 | Schwartz et al. | |

FOREIGN PATENT DOCUMENTS

| | | |
|---|---|---|
| WO | 2002/057422 | 7/2002 |
| WO | 2011/100493 | 8/2011 |

OTHER PUBLICATIONS

Kremsky, Jonathan N., et al. "Immobilization of DNA via oligonucleotides containing an aldehyde or carboxylic acid group at the 5' terminus." Nucleic acids research 15.7 (1987): 2891-2909.*
Dirksen, A. et al., "Bisaryl Hydrazones as Exchangeable Biocompatible Linkers," Angew. Chem. Int. Ed. 2010, 49, 2023-2027.
Haugland, "Molecular Probes Handbook," 6th Edition, Eugene, OR, USA, 110 pages.
Lewis, Patrick T., Notice of Allowance, U.S. Appl. No. 14/717,312, United States Patent and Trademark Office, dated Nov. 9, 2016, 6 pages.
Nielsen, P., et al., "Sequence-Selective Recognition of DNA by Strand Displacement with a Thymine-Substituted Polyamide," Science 1991, 254, 1497-1500.
Solulink, "Antibody-Oligonucleotide All-in-one Conjugation Kit User Manual," Catalog No. A-9202-001, V06, 18, 10, XP002712170, URL:http://search.cosmobio.co.jp/cosmo_search_p/search_gate2/docs/SLK_/A9202001.20100707.pdf [retrieved from Internet on Sep. 3, 2013], Jan. 1, 2009.
Waugh, D.S., "Making the most of affinity tags", Trends in Biotechnology, Jun. 2005, vol. 23, Issue 6, pp. 316-320.
Weinburg, Suzanna, International Search Report and Written Opinion, European Patent Office, PCT/US2012/049339, dated Sep. 13, 2013, pp. 1-12.
West, et al., "Reversible Covalent Chemistry in Drug Delivery", Current Drug Discovery Technologies, (Feb. 2005), 123-150.
York, et al., "Highly parallel oligonucleotide purification and functionalization using reversible chemistry", Nucleic Acids Research, vol. 40, No. 1, e4, XP55077272, Oct. 29, 2011, 1-7.

* cited by examiner

*Primary Examiner* — Patrick T Lewis
(74) *Attorney, Agent, or Firm* — Gavrilovich, Dodd & Lindsey LLP

(57) ABSTRACT

Embodiments of the present disclosure include methods and compositions for functionalizing molecules, such as oligonucleotides, with functional groups, including polyhistidine tags useful in affinity methods. Some embodiments include methods for modifying and purifying complex mixtures of molecules by exchange of functional tags.

14 Claims, 14 Drawing Sheets ically useful group, using one or more reversible chemical steps. The molecules of interest can be, for example, biological molecules (biomolecules) such as polypeptides or polynucleotides, where a group on the molecule is replaced with a purification tag suitable for IMAC purification methods. Functionalized oligonucleotides are thereby provided with tags such as polyhistidine (His-oligos) and biotin (biotin-oligos) in the form of single oligos or in complex pools.

FUNCTIONALIZATION AND PURIFICATION OF MOLECULES BY REVERSIBLE GROUP EXCHANGE

CROSS REFERENCE TO RELATED APPLICATIONS

The present application is a Continuation of U.S. patent application Ser. No. 16/414,593, filed May 16, 2019, which is a Continuation of U.S. patent application Ser. No. 15/431,470, filed Feb. 13, 2017, issued as U.S. Pat. No. 10,294,258, which is a Continuation of U.S. patent application Ser. No. 14/717,312 filed May 20, 2015, issued as U.S. Pat. No. 9,598,453, which is a Continuation of U.S. patent application Ser. No. 13/565,400 filed Aug. 2, 2012, issued as U.S. Pat. No. 9,040,678 on May 26, 2015, which claims priority to U.S. Provisional Patent Application Ser. No. 61/515,663 filed Aug. 5, 2011, all of which are incorporated herein by reference in their entireties.

BACKGROUND

Immobilized metal ion affinity chromatography (IMAC) is widely used, for example for protein purification, exploiting the ability of certain amino acid sequences to form a claw-like configuration around the exposed electrons of a metal ion. When polypeptides contain a suitable amino acid motif, such as a series of histidines (polyhistidine), the amino acids of the motif can form coordinate bonds around metal ions, such as $Ni^{2+}$ or $Co^{2+}$, that are present on an IMAC chromatography surface.

This binding property is particularly useful when a polypeptide of interest contains (or is recombinantly engineered to contain) the motif. Even when the polypeptide is in a complex mixture like an expression cell lysate, the motif can specifically grip the metal ions of the IMAC surface, allowing other components of the mixture to be removed. Because the grip of the coordinate bonding can be reversed, the recombinant polypeptide can then be selectively released from the surface and collected in a purified state. The motif thus serves as a "purification tag" for controlled binding, washing and release of the polypeptide using the IMAC surface. Unlike other chromatography methods that are limited by the number and expense of specialized affinity groups that can be affixed to the matrix. IMAC surfaces can offer bulk densities of metal ions, making such methods efficient and scalable.

While generating polypeptides of interest with an attached motif is straightforward with the tools of recombinant DNA technology, there are practical barriers to attaching them to other classes of molecules of interest, especially when attachment is desired for specific locations on a molecule, or when several molecules are synthesized as a pool and are to be purified in parallel. Thus, IMAC chromatography methods have been unavailable for purification and handling of other molecules, for example oligonucleotides (usually shortened to "oligos"), which are essential for most biotechnological applications. Moreover, there is a need for methods for obtaining the molecules for use in the purification methods, for improved methods for purifying the products, and for the ability to manipulate molecules in general by attaching purification tags and other convenient functional groups by a broadly applicable chemistry.

SUMMARY

Embodiments as disclosed herein relate to methods for modifying molecules of interest by exchange of one group of the molecule with a different, functionally useful group, using one or more reversible chemical steps. The molecules of interest can be, for example, biological molecules (biomolecules) such as polypeptides or polynucleotides, where a group on the molecule is replaced with a purification tag suitable for IMAC purification methods. Functionalized oligonucleotides are thereby provided with tags such as polyhistidine (His-oligos) and biotin (biotin-oligos) in the form of single oligos or in complex pools.

Some embodiments include methods for generating and enriching oligonucleotides useful for the purification methods of the disclosure. The products of some of the methods described herein can be used in a variety of applications.

BRIEF DESCRIPTION OF THE DRAWINGS

FIG. 14A is a bar graph showing the amount of excess biotinylated oligo remaining in supernatant after streptavidin pull-down. FIG. 14B and FIG. 14C are bar graphs showing that a large spike of biotinylated oligos did not adversely affect the enrichment or coverage when ExoI was used in the assay. FIG. 14D is a bar graph showing enrichment using a biotinylated oligo pool of 55 k complexity, with and without ExoI in the assay.

DETAILED DESCRIPTION

Reversible Chemistry for Exchanging Groups

Figure 1:
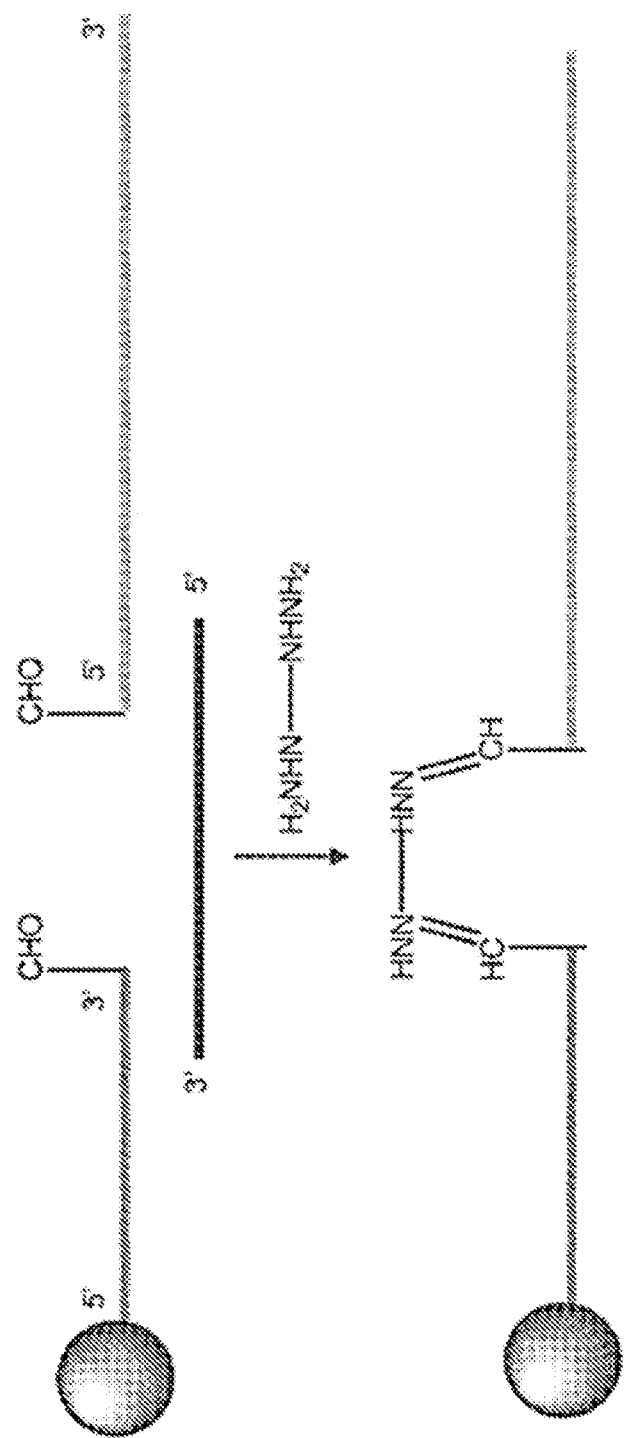
FIG. 1 depicts a method for sequence-specific ligation of two aldehyde-oligos by using a bridging oligo and a linking reagent.

Embodiments of the present disclosure provide broadly applicable methods for modifying molecules that include exchanging one group on a molecule for a desired functional group, such as a tag for facilitating purification of the molecule. After use, the tag can be removed, or optionally the tag can be further exchanged for a second functional group, such as a useful affinity tag or a label tag, for example. The convenient exchange of groups is effected by reversible reactions where equilibrium conditions are controlled at each stage to direct the reaction forward or reverse as desired. After the functionalization, the addition of the functional group can be reversed by the same exchange reaction, but under different equilibrium conditions. Moreover, a functional group added to the molecule can be itself exchanged by subsequent exchange reactions.

Molecules of Interest

A molecule of interest can be any molecule with an exchangeable group for use in embodiments disclosed herein, including inorganic molecules or molecules of non-biological origin. Also useful are "biomolecules." meaning naturally occurring or artificially produced biochemical molecules. Molecules include polypeptides, such as proteins or peptides, amino acids, and derivatives thereof; lipids, fatty acids and the like, and derivatives thereof; carbohydrates, complex saccharides (e.g. oligosaccharides, polysaccharides, glycoconjugates, etc.), monosaccharrides and the like, and derivatives thereof: nucleic acids (polynucleotides of any length, including oligonucleotides), nucleotides, nucleosides, purines, pyrimidines and the like, and derivatives thereof; and any other molecules that may be a constituent of a biological sample. Molecules of interest may be a mixed polymer of two or more of the various molecules listed above. Other biopolymers include known intracellular mediators, co-factors and the like, macromolecular structures and/or assemblies (e.g. cytoskeletal elements, centrioles, chromatin lipid rafts, signal transduction completes), and cytosol.

In some embodiments, a molecule of interest is a different class of molecule than many or all of the other molecules in a mixture. For example, if the molecule of interest is a nucleic acid, molecules of different classes would include molecules comprising amino acids, molecules comprising carbohydrates and/or molecules comprising lipids. In other embodiments, a molecule of interest is a different type of molecule than many or all of the other molecules in a mixture. For example, if the molecule of interest is a nucleic acid having a certain sequence, molecules of different types would include nucleic acids having significantly different sequences. An example of significantly different sequences is sequences that have one or more nucleotide substitutions at the same or similar nucleotide positions.

Polynucleotides

As used herein, the terms "polynucleotide", "oligo", "nucleic acid", and "nucleic acid sequence" are generally used interchangeably and include single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counterions. e.g. $H^+$, $NH_4^+$, trialkylammonium, tetraalkylammonium, $Mg^{2+}$, $Na^+$ and the like. The nucleotide monomer units may comprise any of the nucleotides described herein, including naturally occurring nucleotides and nucleotide analogs.

Nucleic acids include genomic DNA, cDNA, hnRNA, mRNA, rRNA, tRNA, cRNA, alternatively spliced mRNA, small nucleolar RNA (snoRNA), microRNAs (miRNA), small interfering RNAs (siRNA), piwi RNAs (piRNA), any form of synthetic or modified RNA, fragmented nucleic acid, nucleic acid obtained from subcellular organelles such as mitochondria or chloroplasts, and nucleic acid obtained from microorganisms or DNA or RNA viruses that may be present on or in a biological sample.

In nucleic acid sequences described herein, "A" denotes deoxyadenosine or adenosine. "C" denotes deoxycytidine or cytidine, "G" denotes deoxyguanosine or guanosine, "T" denotes deoxythymidine or thymidine, and "U" denotes deoxyuridine or uridine. For RNA, the deoxyribose is replaced with ribose in the nucleotide monomers. Nucleic acids may be composed of a single type of sugar moiety, as in the case of RNA and DNA, or mixtures of different sugar moieties, as in the case of RNA/DNA chimeras.

Nucleic acid sequences herein are generally shown in the 5'-to-3' orientation from left to right, unless otherwise apparent from the context or expressly indicated differently. A functional group described as being in the 5' direction of a nucleic acid (such as a 5'-biotin-oligo) indicates that the group is attached at or near the 5' terminus of a nucleotide or nucleic acid (e.g. directly or indirectly via the 5'-0 or 5'-OH), rather than at or near the 3'-terminus. Likewise a 3'-functional group is attached at or near the 3' terminus of the nucleotide or polynucleotide.

Nucleic acids may vary in length and may be intact or full-length molecules or fragments or portions of larger nucleic acid molecules. Nucleic acids can also be partial or full-length copies of nucleic acids derived from genomic nucleic acids and/or other sources. In particular embodiments, a nucleic acid can comprise at least about 2 nucleotides, at least about 3 nucleotides, at least about 4 nucleotides, at least about 5 nucleotides or more than 5 nucleotides. In particular embodiments, a nucleic acid can comprise at least about 5 nucleotides, at least about 10 nucleotides, at least about 20 nucleotides, at least about 30 nucleotides, at least about 40 nucleotides, at least about 50 nucleotides, at least about 60 nucleotides, at least about 100 nucleotides, at least about 150 nucleotides, at least about 200 nucleotides, at least about 250 nucleotides, at least about 500 nucleotides, or at least about 1.000 nucleotides. In more embodiments, a nucleic acid can comprise from about 150 to about 4000 nucleotides, from about 500 to about 3,000 nucleotides, or from about 1000 nucleotides to about 2000 nucleotides, 3000 nucleotides, 4000 nucleotides, 5000 nucleotides, 6000 nucleotides, 7000 nucleotides, 8000 nucleotides, 9000 nucleotides, or about 10,000 nucleotides in length. Alternatively or additionally, a nucleic acid can comprise no more than about 100 nucleotides, no more than about 250 nucleotides, no more than about 500 nucleotides, no more than about 1000 nucleotides, no more than about 5000 nucleotides, no more than about 10.000 nucleotides, or no more than about 100,000 nucleotides.

As used herein, the term "nucleotide analogs" can refer to synthetic analogs having modified nucleotide base portions, modified pentose portions, and/or modified phosphate portions, and, in the case of polynucleotides, modified internucleotide linkages, as generally described elsewhere (e.g. Scheit. Nucleotide Analogs (John Wiley 1980); Englisch, Angew. Chem. Int. Ed. Engl. 30:613-29 (1991); Agarwal, Protocols for Polynucleotides and Analogs (Humana Press, 1994): and Verma and Eckstein, Ann. Rev. Biochem. 67:99-134 (1998), all of which are incorporated herein by reference in their entireties.

The term "comprising" as used herein is synonymous with "including," "containing," or "characterized by," and is inclusive or open-ended and does not exclude additional, unrecited elements or method steps.

As used herein the term "at least a portion", "a portion thereof" and/or grammatical equivalents thereof can refer to any fraction of a whole amount. For example, "at least a portion" can refer to at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, 99.9% or 100% of a whole amount.

Generally, modified phosphate portions comprise analogs of phosphate where the phosphorus atom is in the +5 oxidation state and one or more of the oxygen atoms is replaced with a non-oxygen moiety such as sulfur. Exemplary phosphate analogs include phosphorothioate, phosphorodithioate, phosphoroselenoate, phosphorodiselenoate, phosphoroanilothioate, phosphoranilidate, phosphoramidate, and boronophosphates, with any associated counterions, e.g. $H^+$, $NH_4^+$, and $Na^+$. Examples of modified nucleotide base portions include 5-methylcytosine (5mC); C-5-propynyl analogs including C-5 propynyl-C and C-5 propynyl-U; 2,6-diaminopurine (also known as 2-amino adenine or 2-amino-dA); hypoxanthine, pseudouridine, 2-thiopyrimidine, isocytosine (isoC), 5-methyl isoC, and isoguanine (isoG; see, e.g. U.S. Pat. No. 5,432,272, incorporated by reference). Exemplary modified pentose portions include locked nucleic acid (LNA) analogs including Bz-A-LNA, S-Me-Bz-C-LNA, dmf-G-LNA, and T-LNA (see, e.g. The Glen Report, 16(2):5 (2003); Koshkin et al., Tetrahedron Letters 54:3607-30 (1998), incorporated herein by reference in its entirety), and 2'- or 3'-modifications where the 2'- or 3'-position is hydrogen, hydroxyl, alkoxy (e.g. methoxy, ethoxy, allyloxy, isopropoxy, butoxy, isobutoxy, and phenoxy), azido, amino, alkylamino, fluoro, chloro, or bromo. Modified internucleotide linkages include phosphate analogs, analogs having achiral and uncharged intersubunit linkages (e.g. Sterchak et al., Organic Chem., 52:4202 (1987), incorporated herein by reference in its entirety), and uncharged morpholino-based polymers having achiral intersubunit linkages (see, e.g. U.S. Pat. No. 5,034,506, incorporated herein by reference in its entirety). Some internucleotide linkage analogs include morpholidate, acetal, and polyamide-linked heterocycles. In one class of nucleotide analogs known as peptide nucleic acids (including pseudo-complementary peptide nucleic acids ("PNA")), a conventional sugar-and-internucleotide linkage is replaced with a 2-aminoethylglycine amide backbone polymer. See, e.g. Nielsen et al., Science. 254:1497-1500 (1991); Egholm et al., J. Am. Chem. Soc., 114:1895-1897 (1992); Demidov et al., Proc. Natl. Acad. Sci. USA 99:5953-58 (2002); Nielsen (ed.). Peptide Nucleic Acids: Protocols and Applications (Horizon Bioscience 2004), all of which are incorporated herein by reference in their entireties.

Molecules from Biological Samples

Molecules useful in disclosed embodiments can be provided by a variety of means, such as by purification from biological samples. As used herein, a "biological sample" can refer to a plurality of molecules that include a molecule of interest. In some embodiments, a biological sample can comprise a library or mixture of compounds. Biological samples can be derived from biological and non-biological origins. For example, biological samples can include a blood sample, biopsy specimen, tissue explant, organ culture, biological fluid or any other tissue or cell preparation, or fraction, derivative, or isolate therefrom, from a subject or a biological source. The subject or biological source may be a human or non-human animal, including mammals and non-mammals, vertebrates and invertebrates, and may also be any other multicellular organism or single-celled organism such as a eukaryotic (including plants and algae) or prokaryotic organism, archaeon, microorganism (e.g., bacteria, archaea, fungi, protists, viruses), aquatic plankton, a primary cell culture or culture adapted cell line including genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, stem cells, germ cells (e.g. sperm, oocytes) and the like. For example, nucleic acids may be obtained from primary cells, cell lines, freshly isolated cells or tissues, frozen cells or tissues, paraffin embedded cells or tissues, fixed cells or tissues, and/or laser-dissected cells or tissues. In certain embodiments, the nucleic acids may be derived, purified, or isolated from any known prokaryotic or eukaryotic organism or virus.

Synthetic Polynucleotides of Interest

Methods for providing synthetic nucleic acids are well known in the art. For example, in some methods, nucleoside phosphoramidites can be utilized. Such nucleoside phosphoramidites are examples of monomer reagents that may be utilized with the methods, from biological samples. In some embodiments, nucleoside phosphoramidates include derivatives of natural or synthetic nucleosides in which protection groups (sometimes referred to a blocking groups) are added to reactive exocyclic amine and hydroxyl groups, and in which an N,N-diisopropyl phosphoramidite group is attached to the 3'-hydroxyl group of each nucleoside. Examples of protecting groups include acid-labile dimethoxytrityl (DMT) groups.

Nucleic acids can also be provided as products of chemical or enzymatic amplification reactions, such as a polymerase chain reaction (PCR). If desired, amplification products can be produced having an exchangeable group (such as an aldehyde) by using forward or reverse primers incorporating the exchangeable group so that amplicons are produced having the exchangeable group.

In some synthesis methods, full-length products can be modified for example by an additional final group (such as by a formylindole phosphoramidite modifier during synthesis) to serve as a terminating group, as well as a useful means for distinguishing full-length from incomplete synthesis products.

Functional Tags

The present disclosure provides molecules of interest that have groups that can serve as functional tags. In some embodiments, a functional tag can include a chemical and/or biological moiety that provides one or more desired functional characteristics.

The functional tags described herein can be present at any location of a molecule of interest. In some embodiments, a molecule of interest comprising a polypeptide or protein can include a functional tag at the C-terminal end, at an intermediate amino acid, or at the N-terminal end. In other embodiments, a molecule of interest comprising a nucleic acid may include a functional tag at the 5' end, at an intermediate nucleotide, or at the 3' end of the nucleic acid.

For example, a functional tag can be an aldehyde group present on an oligo of interest, such as on the 5'-OH or the 3'-OH, or as part of a larger moiety, such as a formylindole.

Other examples of functional tags include label tags and affinity tags, which can serve as purification tags.

Label Tags

As used herein, the term "label tag" refers to any identifiable tag, label, or group. Many different species of label tags can be used in the embodiments herein, individually or in combination with one or more other label tag species. Examples of label tags include fluorophores, radioisotopes, chromogens, enzymes, antigens including epitope tags, semiconductor nanocrystals such as quantum dots, heavy metals, dyes, phosphorescence groups, chemiluminescent groups, electrochemical detection moieties, binding proteins, phosphors, rare earth chelates, transition metal chelates, near-infrared dyes, electrochemiluminescence labels, and mass-spectrometer-compatible reporter moieties, such as mass tags, charge tags, and isotopes.

In certain embodiments, a label tag can emit a signal, which can be fluorescent, a chemiluminescent, a bioluminescent, a phosphorescent, a radioactive, a calorimetric, or an electrochemiluminescent signal, for example. Other label tags include spectral labels such as fluorescent dyes (e.g. fluorescein isothiocyanate, Texas red, rhodamine), radiolabels (e.g. $^{3}H$, $^{125}I$, $^{35}S$, $^{14}C$, $^{32}P$, $^{33}P$), enzymes (e.g. horseradish peroxidase, and alkaline phosphatase) spectral calorimetric labels such as colloidal gold or colored glass or plastic (e.g. polystyrene, polypropylene, latex) beads; magnetic, electrical, thermal labels; and mass tags. Label tags can also include magnetic particles. More label tags include 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes and flavin. Individual fluorescent compounds that have functionalities for linking a label to a molecule of interest include dansyl chloride; fluoresceins such as 3,6-dihydroxy-9-phenylxanthydrol; rhodamineisothiocyanate; N-phenyl 1-amino-8-sulfonatonaphthalene; N-phenyl 2-amino-6-sulfonatonaphthalene; 4-acetamido-4-isothiocyanato-stilbene-2,2'-disulfonic acid; pyrene-3-sulfonic acid; 2-toluidinonaphthalene-6-sulfonate; N-phenyl-N-methyl-2-aminoaphthalene-6-sulfonate; ethidium bromide; stebrine; auromine-0,2-(9'-anthroyl)palmitate; dansyl phosphatidylethanolamine; N,N'-dioctadecyloxacarbocyanine: N,N'-dihexyloxacarbocyanine; merocyanine, 4-(3'-pyrenyl)stearate; d-3-aminodesoxy-equilenin; 12-(9'-anthroyl)stearate; 2-methylanthracene; 9-vinylanthracene; 2,2'-(vinylene-p-phenylene)bisbenzoxazole; p-bis(4-methyl-5-phenyl-2oxazolyl))benzene; 6-dimethylamino-1,2-benzophenazin; retinol; bis(3'-aminopyridinium) 1,10-decandiyldiiodide; sulfonaphthylhydrazone of hellibrienin; chlorotetracycline; N-(7-dimethylamino-4-methyl-2-oxo-3-chromenyl)maleimide; N-(p-(2benzimidazolyl)-phenyl)maleimide; N-(4-fluoranthyl)maleimide; bis(homovanillic acid); resazarin; 4-chloro7-nitro-2,1,3-benzooxadiazole; merocyanine 540: resorufin; rose bengal; 2,4-diphenyl-3(2H)-furanone, fluorescent lanthanide complexes, including those of Europium and Terbium, fluorescein, rhodamine, tetramethylrhodamine, eosin, erythrosin, coumarin, methyl-coumarins, quantum dots (also referred to as "nanocrystals": see U.S. Pat. No. 6,544,732, hereby incorporated by reference in its entirety), pyrene, Malachite green, stilbene. Lucifer Yellow, Cascade Blue™, Texas Red, Cyanine dyes (such as Cy3 and Cy5). Alexa dyes, phycoerythin, bodipy, and others described in Haugland et al. (eds.), Handbook of Fluorescent Probes and Research Chemicals (6th ed. 1996), expressly incorporated by reference herein. More examples of label tags include, but are not limited to, affinity labels such as biotin, avidin, streptavidin, digoxigenin, antibody Fc domain, protein A, protein G, antibody antigen-binding domain, and lectins.

Label tags can be selected for inclusion in the presently disclosed compositions and methods depending on the particular parameter or parameters that may be of interest for particular molecules in biological samples in particular applications. Examples of parameters that may be detected by some label tags include detection of the presence of one or more of an amine, an alcohol, an aldehyde, water, a thiol, a sulfide, a nitrite, avidin, biotin, an immunoglobulin, an oligosaccharide, a nucleic acid, a polypeptide, an enzyme, a cytoskeletal protein, a reactive oxygen species, a metal ion, pH, $Na^+$, $K^+$, $Cl^-$, a cyanide, a phosphate, selenium, a protease, a nuclease, a kinase, a phosphatase, a glycosidase, and a microbial contaminant.

Affinity Tags

Some embodiments disclosed herein include methods for isolating a molecule of interest. In some such methods, a molecule of interest comprises a purification tag that contacts a binding partner. The association of the purification tag and binding partner may be used to separate the molecule of interest from a mixture of molecules.

A purification tag can comprise moieties with the same or similar structures. In certain embodiments, the tagging moiety of an affinity tag can be associated with a functional tag directly by a single bond or via a linkage of stable chemical bonds, in linear, branched or cyclic arrangements, optionally including single, double, triple bond, aromatic carbon-carbon bonds, as well as carbon-nitrogen bonds, nitrogen-nitrogen bonds, carbon-oxygen bonds, carbon-sulfur bonds, phosphorus-oxygen bonds, phosphorus-nitrogen bonds, and any combination thereof. In certain embodiments, the association between the tagging moiety and functional tag comprises ether, thioether, carboxamide, sulfonamide, urea or urethane moieties. In preferred embodiments, the linkage comprises a polyalkylene chain, i.e., a linear or branched arrangement of carbon-carbon bonds. In other embodiments, the linkage comprises a polyalkylene oxide chain, including a polyethylene glycol moiety.

Examples of affinity tags include, but are not limited to, biotin, digoxigenin (Dig), dinitrophenol (DNP), zinc fingers, fluorinated polymers, and polypeptide sequences such as polyhistidine motifs.

Affinity Substrates

Some embodiments disclosed herein can be used with solid substrates having an affinity for a functional group. In some embodiments, the binding partner may be immobilized on an affinity substrate. As used herein the term "affinity substrate" can refer to an immobile matrix or support bound to a binding partner that is capable of forming a strong and preferably reversible interaction with the purification tag of a molecule. An affinity substrate can include a resin, a bead, a particle, a membrane, a gel. The binding partner recognizes or binds to the purification tag specifically. Specific binding partners will depend on the affinity tag, but include charged moieties and one member of a binding pair such as receptor-ligand, antibody-antigen, carbohydrate-lectin, and biotin-streptavidin.

Preferably, the purification tag binds to the affinity substrate with an affinity constant ($K_a$) of at least about $10^3$ $M^{-1}$, $10^4$ $M^{-1}$, preferably at least about $10^5$ $M^{-1}$, more preferably at least about $10^6$ M$^{-1}$, still more preferably at least about $10^7$ M$^{-1}$ and even more preferably at least about $10^8$ M$^{-1}$ or stronger affinity. Affinity constants may be determined using well known techniques including any number of standard binding assays or techniques, for example, those described by Scatchard et al., Ann. N.Y. Acad. Sci. 51:660 (1949); and R. K. Scopes, Protein Purification: Principles and Practice (Springer-Verlag 1987, incorporated by reference herein in their entireties).

IMAC Resins

In certain embodiments, the binding partner comprises a metal ion bound to an immobile matrix via coordination bonds which can be useful in ion metal affinity chromatography (IMAC). Due to the availability of metal ions to the solution phase, the binding capacities of IMAC resins can be unusually high. The amount of IMAC substrate can be controlled to scale up a method disclosed herein, or to serve as a control on the amount of product yield, if desired. IMAC surfaces are available in various formats (bulk slurries, pre-loaded columns, spin columns, coated 96-well plates, magnetic beads for example) and the term "resin" is used herein to mean any of these formats. The convenient format of IMAC resins is amenable to highly parallel formats and automation for processing many individual molecules or pools of molecules.

Examples of metal ions that have specific recognition capability for purification tags, such as polyhistidines, include $Ni^{2+}$ and $Co^{2+}$. Suitable IMAC resins include commercially available kits such as Ni Sepharose® (Amersham Bioscience), Ni-NTA-agarose (Qiagen), His60 Ni Superflow™ (Clontech Laboratories, Inc.), HisPur™ cobalt or nickel resins (Pierce Chemical Co.), and TALON®His-Tag purification resin (Clontech) to name a few.

A molecule of interest can have one or more, for example, two or more different affinity tags (such as a His tag and a biotin) and the affinity substrate having one or more corresponding binding agents (such as a bifunctional IMAC resin having both metal ions and streptavidin for the exemplary His and biotin tag, respectively). Such an exemplary bifunctional combination of binding affinities allows much more specific binding in the methods of the disclosure. As discussed above IMAC resins have found use in protein purification methods, but the present disclosure provides methods for using IMAC resins for purification of any molecule of interest having an exchangeable group. Moreover, in some embodiments a molecule of interest may have two or more, three or more, four or more, etc. affinity tags which are the same, for example are the same functionally, such as two or more biotins, two or more His tags, and the like. Further, if there are a plurality of affinity tags (e.g., two or more, etc.), there could be a disproportionate amount of the different tags, for example more biotin tags than His tags than digoxigenin tags, for example.

As used herein, the terms "purifying," "isolating," "separating," (and their grammatical forms) are used interchangeably and refer to substantially or essentially enriching a mixture for the molecule of interest. In some embodiments, enriching a mixture for a molecule of interest includes removing components (collectively "contaminants) of a mixture other than a molecule of interest. In certain embodiments, "isolating a nucleic acid" may refer to separating an oligo (e.g. a full-length oligo) from other oligos (e.g. truncated oligos, fragmented oligos, etc.) in a reaction mixture following a chemical or enzymatic oligo synthesis. In other embodiments, "isolating a nucleic acid" may be purifying a nucleic acid from the nucleotide sequences that flank it in a naturally occurring state, such as a DNA fragment that has been separated or removed from the sequences that are normally adjacent to the fragment. In yet other embodiments, "isolating a molecule" may refer to extracting a molecule from a cell, tissue, or organism such that it is no longer present in the cell, tissue or organism in its natural state. It will be appreciated that purifying does not require that the molecule of interest be completely separated from all contaminants, but can refer to increasing the proportion of one or more particular molecules in a mixture of molecules relative to contaminants, including purification so the molecule is substantially free of contaminants.

As used herein, "substantially free of contaminants" refers to compositions having less than about 75% contaminating molecules, less than about 50% contaminating molecules, less than about 25% contaminating molecules, less than about 20% contaminating molecules, less than about 15% contaminating molecules, less than about 10% contaminating molecules, less than about 5% contaminating molecules, less than about 4% contaminating molecules, less than about 3% contaminating molecules, less than about 2% contaminating molecules, less than about 1% contaminating molecules.

Non-Full-Length Oligonucleotides

Some methods provided herein are advantageous in purifying full-length synthesized oligos, especially those synthesized by stepwise addition of monomeric units. For example, in nature (and in many older chemical methods), polynucleotides are typically synthesized in the 5'-to-3' direction. However, a particularly useful method for obtaining synthetic oligonucleotides is stepwise synthesis in the 3'-to-5' direction. For some synthetic methods, stepwise addition can result in a mixture of full-length nucleic acids (e.g. n-mer) and nucleic acids shorter than full-length, due to inefficiencies during individual synthetic steps. These can include side products resulting from incomplete deprotection or modification, or protecting groups cleaved from the nucleotide bases after synthesis. Other undesirable side products result from incomplete synthesis that are less then full-length (e.g. (n-1)-mer, (n-2)-mer, (n-3)-mer, etc).

Oligos can be synthesized by methods such as phophoramidite synthesis such that only full-length oligos incorporate a terminal nucleotide comprising an aldehyde group. However, the final incorporation is not necessarily 100% efficient, and the number of oligos having the aldehyde group can be, for example 60%, 70%, 80%, or 90%.

When the functional tag is added to a polymer as the first or last step of full-length synthesis, the absence of the tag can serve as an indicator that the synthesis was not complete for that polymer (e.g. FIG. 3, 210a, 210b, 210c). The presence of the tag indicates that the polymer is full-length, as exemplified by the aldehyde-oligo (200) in FIG. 3. The tag can further function as a means of attachment for easier manipulation.

Solid Phase Attachment

In some embodiments, oligos can be attached to a solid phase surface for case of manipulation, for example in performing chemical reactions on the oligos, washing, and collecting the oligos by detachment from the surface. Oligos can be attached to surfaces, such as beads, by various methods known in the art. Alternatively, aldehyde-oligos used in disclosed embodiments can be attached to a solid phase through the hydrazide reactions discussed in more detail below. In methods disclosed herein, solid phase attachment can be either reversible or irreversible. For example, molecules of interest (e.g., oligonucleotides) can be attached to a solid phase and can be released through reversible chemistries such as released by cleaving a cleavable linker incorporated into a molecule of interest. Further, a molecule of interest could be itself cleaved. Cleavable linkers that could be incorporated into molecules of interest such as oligonucleotides include, but are not limited to, azide groups, alkoxy groups, disulphide groups, diol groups, diazo groups, ester groups, sulfone azide, alyl or silyl ether groups, acid labile groups, Sieber groups, indole groups, t-butyl Sieber groups, electrophilically cleavable groups, nucleophilically cleavable groups, photocleavable groups, cleavage groups that cleave under reductive conditions or oxidative conditions, cleavage via use of safety-catch groups, cleavage by elimination mechanism and metal assisted cleavage groups. Conversely, a molecule of interest could be irreversibly affixed to solid phase supports, such as through covalent binding of the molecule to a substrate either directly or indirectly (e.g., via a linker, etc.). Irreversible affixation of a molecule of interest to a substrate is particularly advantageous for high-capture efficiencies.

In other embodiments, an affinity tag can be irreversibly coupled to a substrate but still comprise a reversible moiety and/or be complexed with a linker that comprises a reversible aspect and/or a molecule of interest that comprises a reversible aspect, or a combination thereof. For example, a molecule of interest could be irreversibly affixed to a solid substrate via, for example, covalent attachment. For example, in some embodiments, an affinity tag comprises irreversible coupling chemistry that irreversibly binds to a solid support, but additionally the affinity tag comprises a reversible sequence (e.g., a cleavable sequence) that allows for release of the molecule of interest from the coupling chemistry. In other embodiments, a linker that links the affinity tag to the molecule of interest comprises a reversible sequence, for example a cleavage group that can be cleaved to release the molecule of interest from the permanently affixed coupling chemistry. In other embodiments, the molecule of interest itself comprises releasable sequences, such as cleavage groups, that can be cleaved to release the molecule of interest from the irreversibly affixed coupling chemistry on the solid support. In some embodiments, an affinity tag/linker/molecule of interest complex can comprise a plurality of irreversible and reversible sequences which can be used, for example, for purification purposes of the molecule of interest from a sample.

A skilled artisan will understand the myriad options available for both reversibly and irreversibly binding a molecule of interest to a substrate.

Reversible Attachment of 5'-Aldehyde Oligos to a Solid Phase

An alternate method for attaching aldehyde-oligos is provided in this disclosure, which enables aldehyde-oligos to be attached or detached from a solid surface by forming a reversible imine (generally $R^1R^2$—C=N—$R^3$) linkage between an aldehyde-oligo and an amine-functionalized surface. Any combination of functionalities that can form an imine bond can be used. For example, an amine can be on the oligo and the aldehyde can be at the surface. The aldehyde can be also a ketone. The amine functionality can be a simple aliphatic amine or a hydrazine. A useful amine functionality is an alkoxyamine, since alkoxyamine-based imines can form a stronger bond than aliphatic-based imines.

In one embodiment a full-length oligo is provided having a 5'-aldehyde moiety. Where the oligo is provided in the form of a 3'-to-5' synthesis reaction product, the final addition can be an aldehyde-containing moiety, so that incomplete synthesis products (non-full-length) lack the aldehyde. The amino-surface can be provided by reaction of 3-aminopropyltrimethoxy silane with a glass surface, e.g. glass beads, a flat glass microscope slide, controlled pore glass (CPG), or amine functionalized polystyrene beads. The aldehyde-oligo is allowed to react with the solid-phase amine, for example in a citrate buffer (pH 6.5), to form a stable imine bond that anchors the oligo to the solid phase. The solid support can be washed to remove any unbound oligo, such as non-full-length synthesis products that lack an aldehyde.

Optionally, the bound oligo can be cleaved from the solid support using acid-catalyzed hydrolysis conditions to regenerate the full-length aldehyde-oligo and the free amine-surface. The oligo can also be cleaved by transamination with an aqueous solution of para-toluenesulfonic acid (p-TsOH or tosylic acid), which can be catalyzed by aniline or scandium (III) trifluoromethanesulfonate (scandium triflate). Yet another cleavage method involves washing the solid support with an amino-functionalized molecule so that the aldehyde transaminates with the non-bound amine, forming an imine on the free aldehyde. It should be noted, however, that this last embodiment does not restore the aldehyde functionality.

The reversible attachment/detachment of oligos to solid surfaces is particularly useful for flow-through synthesis methods. The oligo is synthesized on the amidite-functionalized CPG, cleaved from the CPG with ammonium hydroxide, then immediately neutralized to pH 6, so the oligo-synthesis product is allowed to flow onto the amine-functionalized CPG. Non-full-length oligos do not attach to the amine-CPG and are washed away. If desired, the full-length oligos can be detached and collected for further use.

Bridge Ligation of Aldehyde-Oligonucleotides

Another use for aldehyde-oligos is the sequence-specific ligation of two functionalized oligos to obtain a longer oligo containing a defined combination of sequences. The functionalization can be an aldehyde, although the two oligos can be biotin-oligos, as provided by embodiments, for example those found below.

A specific embodiment is exemplified in FIG. 1, where the first oligo is provided with an aldehyde at the 3' terminus. The second oligo is provided with an aldehyde at the 5'-terminus. As disclosed herein, one or both oligos are optionally immobilized to a solid substrate (such as a bead) to facilitate handling, washing, and collection. Either one or both oligos can also contain additional sequences for use in various applications (such as genotyping, identification, and sequencing reactions) as long as the additional sequences do not interfere with the linking reaction.

By way of example, a bridging oligo is also provided that contains (at its 3' terminus) a first sequence that is complementary to the 3' portion of the first oligo. The bridging oligo also contains (at its 5' terminus) a second sequence that is complementary to the 5' portion of the second oligo. The bridging oligo preferably contains sequence that is sufficient in length to allow sequence-specific hybridization to first and second oligos under similar conditions. The first and second sequences of the linker are allowed to hybridize to the first and second oligos, forming a sequence-specific hybridization complex where the two aldehydes are brought into proximity.

A bifunctional linking reagent is provided that comprises at least two moieties that could react with aldehyde groups, such as a hydrazine or amine moiety. A hydrazine-aldehyde reaction can be catalyzed with a catalyst of aniline and its derivatives. Other useful moieties include, but are not limited to, maleimide-thiol, maleimide-amine, streptavidin-NHS (N-hydroxysuccinimide), isothiocyanate-amine, amine-carboxyl catalyzed by EDC, thiol-thiol, and dialkene (e.g., obtained by a water-soluble methathesis catalyst). A particular reactive aldehyde linker (Aldrich 639958) is

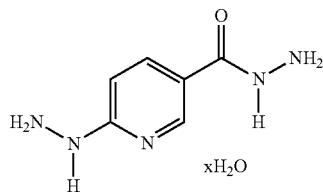 [SMILES: NNC(=O)c1ccc(NN)nc1]

The aldehyde-reactive moieties of the linking reagent are allowed to react with the adjacent aldehydes of the two oligos of the hybridization complex, forming a covalent linkage between the two oligos. Since the hybridization complex can form when the bridging oligo specifically coordinates the combination of the first and second oligos, the ligation can occur only for the two designated oligos of interest.

This method is particularly useful for combinatorial applications using a pool of various first oligos (e.g., with different sequences, such as a set of DNA bar codes) in combination with a pool of various second oligos (e.g., with different sequences, such as an orthogonal set of DNA bar codes, a recognition or detection sequence, or a biologically active sequence). The method allows generation of oligos having a desired combination of first and second oligo sequences by introducing relatively short bridging oligos to coordinate the chemical ligation of different combinations of first and second oligos. For instance, pools of 100-mer first oligos and 400-mer second oligos can be joined to generate specific 500-mers by means of a bridging oligo having two 20-base complementary sequences for specific hybridization. If desired, the ligated oligos can be used while attached to a solid phase, or detached for further use. The skilled artisan will understand that the first and second sequences of the resulting oligos are separated by the covalent linker, so not all biochemical processes (such as polymerase amplification) are feasible across the linker. However, the linker does not affect applications where the first and second sequences need only be present on the same molecule, such as when oligos (and attached beads) are identified by independent binding events. Thus, method disclosed herein provides a rapid and convenient method for generating a combinatorial library of beads having a predefined selection of sequences.

Exchange Reagents

A general method for exchanging groups uses "exchange reagents" that comprise a functional group (as discussed herein) attached to the rest of the molecule by a bond, allowing the functional group exchange with another group on the molecule of interest. If desired, the amount of exchange reagent used can be limited to control the total yield of the final product. According to the application and stage of synthesis, the bond can be irreversible or reversible as desired. An example of an irreversible exchange reagent is a biotin oxo-amine, which appears in the middle portion of FIG. 4.

Examples of reversible exchange reagent are nucleophiles, for example a reagent containing an imine (—C=N—), where the imine serves as a stable, but reversible bond. These reagents can be formed by reaction with hydrazides (generally $(R^1(C=O)R^2-N-N-R^3R^4)$, hydroxylamine ($NH_2OH$) and the like. Useful examples include hydrazones ($R^1R^2C=N-NH_2$) and their derivatives, such as bisarylhydrazones, which are formed between a benzaldehyde and a hydrazinopyridine group. Schiff bases (e.g. $R^1R^2C=N-R^3$ or $HR^2C=N-R^3$) are also useful imine reagents. Yet another reversible reagent is hydrazinic acid (hydrazine with an acyl group). In other embodiments, the exchange reagent contains an electrophile, as long as the reagent can form a reversible bond.

Figure 2A:
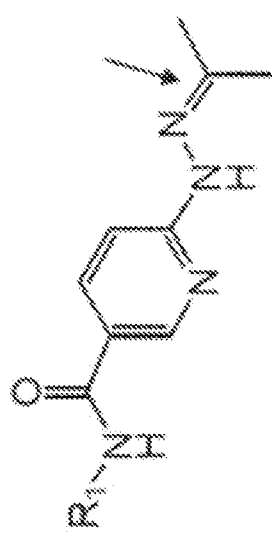
FIG. 2A depicts a useful exchange moiety, 6-hydrazinonicotinate acetone hydrazone ("Hynic")
Figure 2B:
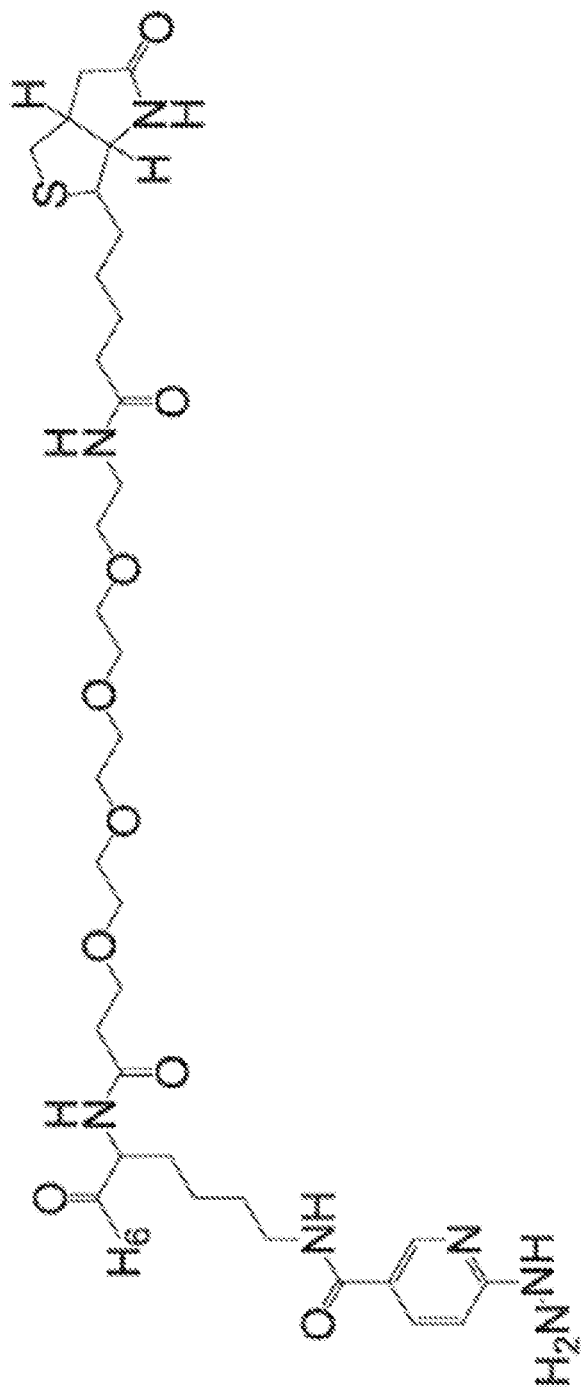
FIG. 2B depicts a bifunctional exchange reagent, His-HyNic-biotin.

The exchange reagent can contain an exchange moiety to facilitate the exchange. A particularly useful exchange moiety is 6-hydrazinonicotinate acetone hydrazone ("HyNic") (Solulink, Inc., San Diego), shown in FIG. 2A, where the arrow indicates the imine bond. A modified version of HyNic can also be used where the dimethyl hydrazone (—NH—N=C(CH$_3$)$^2$) is replaced by a hydrazine (—NH—NH$_2$), thus 6-hydrazinonicotinamide (also referred to herein as HyNic). Other modified versions include replacing the dimethyl hydrazone with a nucleophile such as methyl hydrazone (—NH—N=CH(CH$_3$)) or (—NH—N—CH$_2$). A particular exchange reagent can have a HyNic moiety and a functional group to be exchanged. For example the functional group can be any purification tag such as a polyhistidine, such as a His tag coupled to the exchange reagent via a peptide bond at the N-terminus of the His tag. An exemplary exchange reagent is His-HyNic, where R$_1$ in FIG. 2A is 6 histidine residues. Another useful exchange reagent is biotin-HyNic. Yet another useful affinity tag reagent comprises both a purification tag and a functional group: FIG. 2B shows a His-HyNic-biotin reagent that couples with an aldehyde-labeled oligo to generate an oligo labeled with both His (H$_6$) and biotin.

Reversible Chemistries

One advantage of using a hydrazide group is it can reversibly form the imine bond (—C=N—) when coupled to an aldehyde group to form a relatively stable Schiff base. Other reversible chemistries can also be used in the disclosed method. For example, an imine can be reversibly converted to a ketone or aldehyde, which can be reversibly converted to an enamine. Another example is 2-cyclohexenone, which can be reversibly converted (using CH$_3$NH$_2$) to a β-amino ketone product.

Yet another reversible chemistry that can be used in methods disclosed herein are the various "click chemistry" reactions (e.g. U.S. Pat. Nos. 6,737,236 and 7,427,678, each incorporated herein by reference in its entirety). A useful family of reactions is the azide alkyne Huisgen cycloaddition, which uses a copper catalyst (e.g. U.S. Pat. Nos. 7,375,234 and 7,763,736, each incorporated herein by reference in its entirety). Other reactions include copper-free Huisgen reactions ("metal-free click") using strained alkynes.

The reversible bond is used for exchanging a group on a molecule of interest for a desired functional group, such as a purification tag. The convenient exchange of groups is effected by reversible reactions where equilibrium conditions are controlled at each stage to direct the reaction forward or reverse as desired. Even if thermodynamically disfavored, a reaction can be driven forward by providing excess reactant or by withdrawing product as it is formed (for example by sequestration using phase transition) to allow the reaction to proceed continuously. When desired, the same reaction can be driven in reverse by providing excess product or withdrawing reactant. The manipulation of the direction of reversible reactions at will is thus exploited to exchange functional groups in a chain of reactions to yield a final product.

Functionalization of Molecules with His Tags by Exchange

In the methods provided herein, the molecule of interest comprises an exchangeable group. An exchange reagent is provided, which comprises a functional group attached to an exchange moiety. The molecule of interest is contacted with the exchange reagent under conditions and for a time sufficient for the imine bond to be broken between the exchange moiety and the functional group, and for a new imine bond to form, bonding the functional group to the molecule of interest. Thus, the exchangeable group is replaced with the functional group on the molecule of interest.

Where the molecule of interest in an oligo, the oligo can be single- or double-stranded, and its strandedness can be maintained (e.g., using the appropriate hybridization or denaturation conditions) to obtain single- or double-stranded oligo products.

Figure 3:
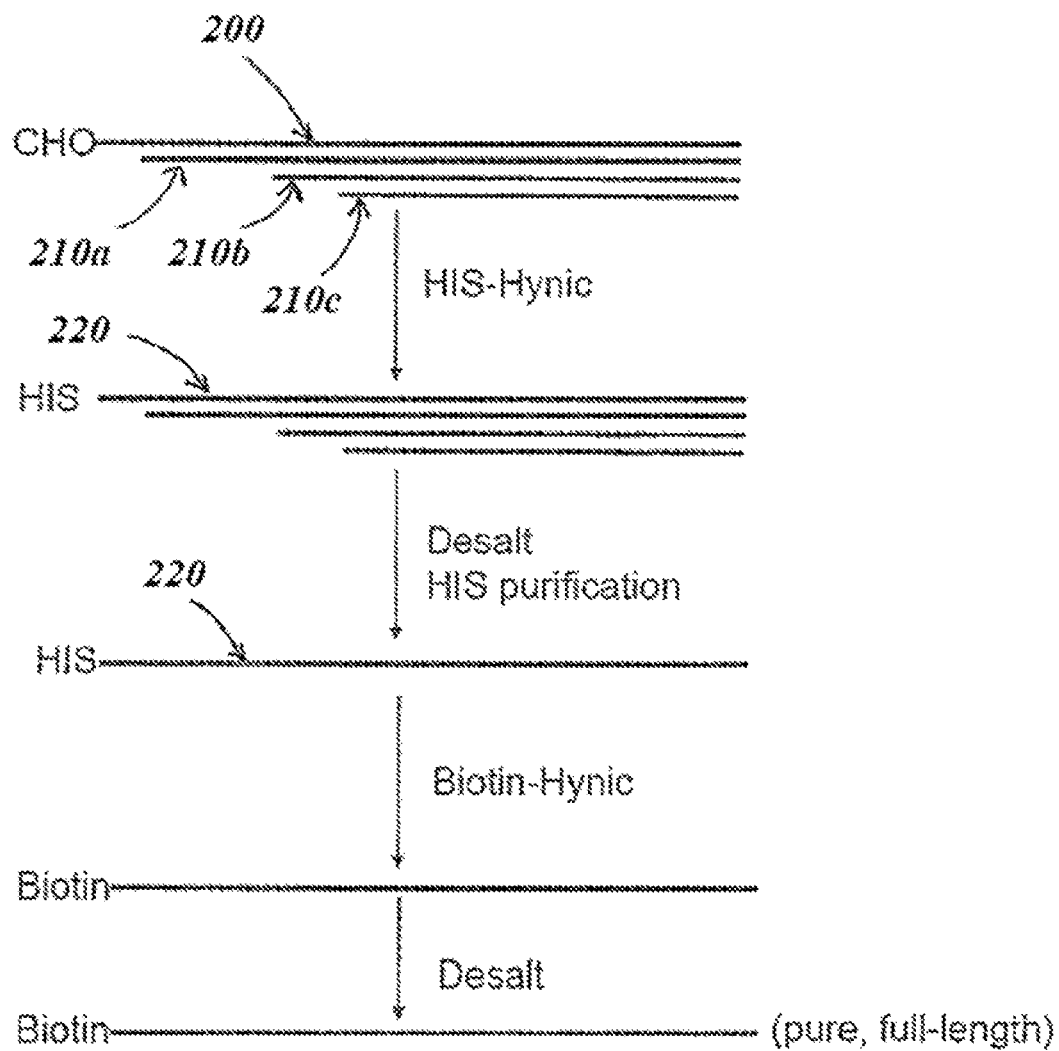
FIG. 3 illustrates an embodiment of a method for functionalization of full-length oligos with biotin, while avoiding functionalization of oligos that are not full-length.
Figure 4:
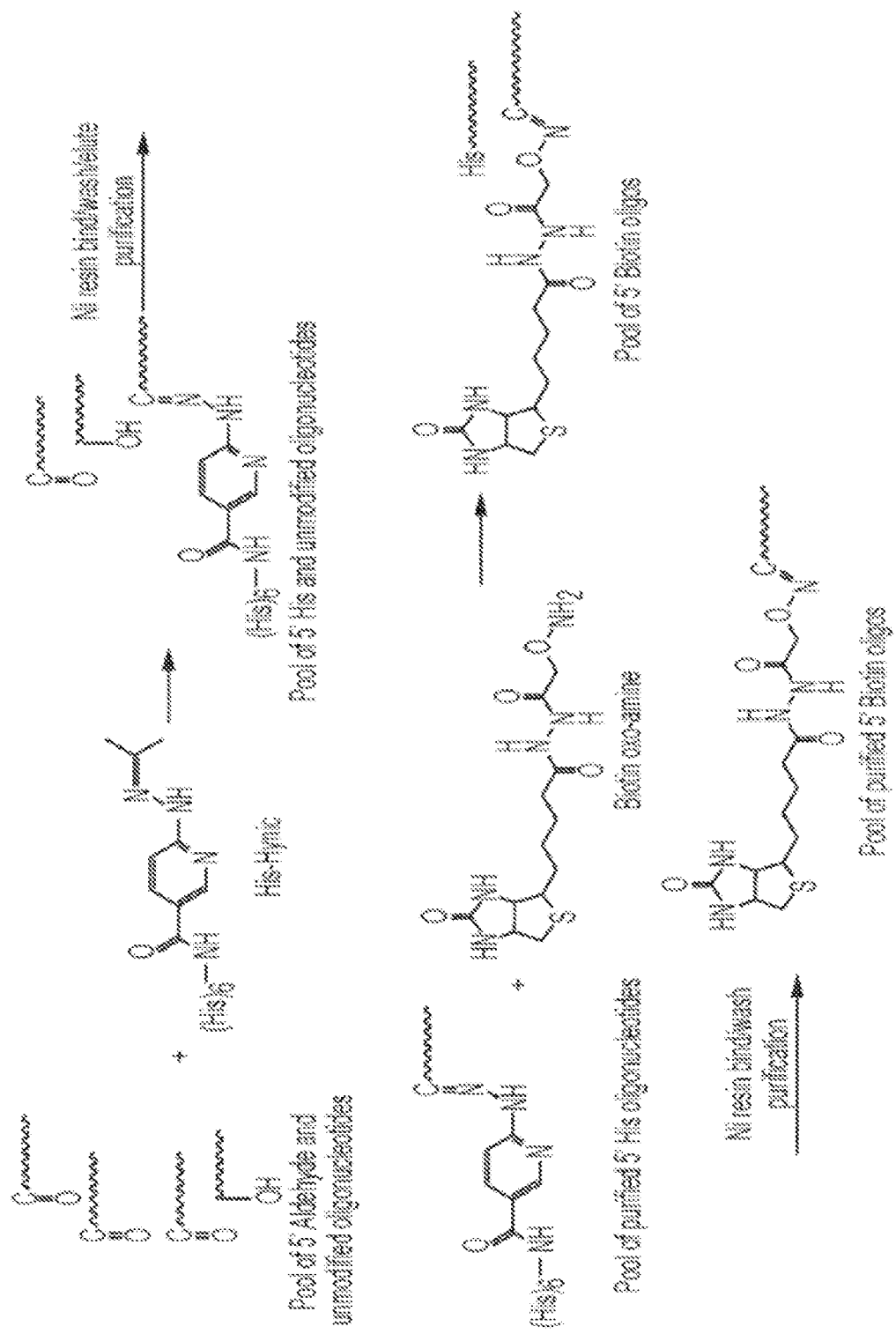
FIG. 4 illustrates particular steps for obtaining a purified pool of biotin-oligos.

An embodiment of the exchange reaction is exemplified in FIG. 3 and FIG. 4, where the molecule of interest is an oligo with an exchangeable aldehyde group (200). The exchange reagent is His-HyNic, which contains an imine, and the exchange moiety is HyNic, and the functional group is polyhistidine (abbreviated $His_6$, $H_6$ or simply His), which can serve as a purification tag in later steps. After the exchange reaction, the His becomes covalently linked to the oligo via a hydrazone (=C—N—NH—) to provide a His-oligo (220). However, oligos that lack the exchangeable aldehyde, such as incompletely synthesized products (210a, 210b, 210c) are not functionalized and lack a His tag. The exchange reaction thus can result in a mixture of full-length His-oligos and non-tagged incomplete products (e.g., contaminants).

IMAC Chromatography

As discussed herein, a particular affinity substrate is an IMAC chromatography surface, such as a chelated nickel resin. The mixture comprising the full length His oligos as exemplified above is allowed to bind to a nickel resin, and the His-tagged molecules are bound to the Ni-column, whereas the untagged incomplete products are washed off. Where the molecule of interest is an oligonucleotide, the wash steps can be made unexpectedly stringent compared to conventional wash steps when purifying polypeptides. For example, a wash of NaOH or urea would denature proteins bound to an affinity substrate, but it does not significantly affect bound oligonucleotides or the polyhistidine motif, and can serve to remove proteinaceous contaminants such as nucleases or any undesirable Ni-binding proteins that may occur naturally in the sample.

The bound His-tagged molecules can be eluted from the Ni-column, for example by competitive elution with metal ions in solution.

Figure 5:
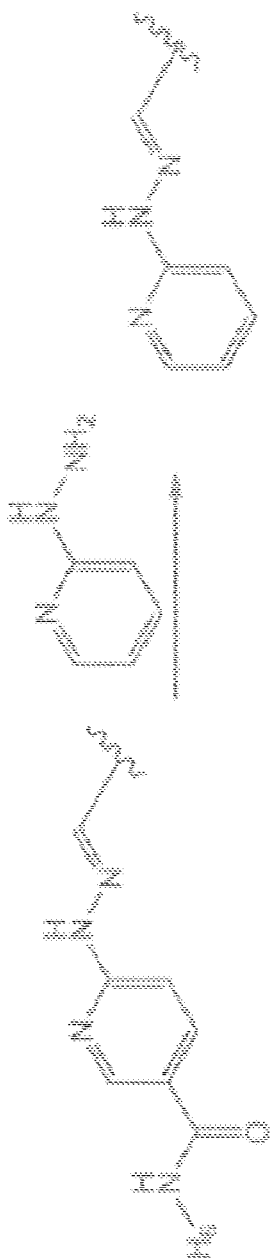
FIG. 5 depicts the removal of the His tag from a His-oligo using 2-pyridine hydrazide aniline.

If desired, methods can include a step that comprises releasing the functional tag (e.g., by cleavage, etc.) to yield a purified molecule. In the example of the hydrazide reaction, an affinity tag can be replaced by reversing the formation of the imine bond via reaction through aldehyde as described herein, while introducing a non-functional moiety in place of the affinity tag. As shown in FIG. 5, for example, the His-HyNic moiety that is coupled to a molecule can be replaced by a non-functional hydrazide moiety by incubating with 2-pyridine hydrazide aniline. The His tag is thus cleaved to generate a substantially pure biotinylated oligo. A His tag can also be removed by endopeptidases, which do not affect oligos, for example. Alternatively, the addition reaction of the functional group can be such as reversed by the same exchange reaction, but under different equilibrium conditions.

Further Exchanges

In certain exchange reactions, the product remains in an exchangeable state that can be exploited for further manipulation, taking advantage of the functionalization.

Accordingly, the products of the exchange reaction or the purification step can be used in one or more subsequent exchange reactions. For example the functional group can itself be exchanged for a second functional group to yield another product, and so forth. In FIG. 3, after obtaining His-oligos (220), a second exchange reagent of biotin-HyNic is used, where HyNic is the exchange moiety and the biotin is the second functional group. The His-tag of the His-oligo is thus replaced with the biotin group to yield a biotin-oligo. Alternatively, the second exchange reagent can be methoxyamine to yield an unlabeled oligo product.

Irreversible Exchanges for End Product

In other embodiments, it can be advantageous to obtain a final product by using a nonreversible exchange at one or more steps. Thus, a method can involve at least one initial exchange (using at least one reversible reaction), followed by a nonreversible exchange so that the final product does not readily revert to an earlier intermediate product. As a result, the final product is obtained in higher yields and with greater stability. A nonreversible exchange step can be facilitated for example by a nucleophile, such as an oxo-amine (—O—$NH_2$), between oligo and functional group (see, e.g. West and Otto, Current Drug Discovery Technologies 2(3):1144-1153 (2005), incorporated herein by reference in its entirety).

As exemplified in FIG. 4, the His-oligos can be reacted with biotin oxo-amine to exchange the His tag for a biotin tag, yielding biotin-oligos. Any residual His-oligos can be separated from biotin-oligo products by passing the mixture through a nickel resin a second time to yield pure biotin-oligos, for example.

Advantages

The simple binding and wash steps of the methods lend themselves to automation. Where the affinity substrate is a chromatography resin in the form of beads, the methods disclosed herein can be readily scaled up, taking advantage of the high binding capacity of IMAC surfaces to functionalize and purify mmol quantities of oligos. Another benefit of this approach is that the relatively low cost of components like HyNic and IMAC resins, which can be readily regenerated after use.

Another significant advantage to methods disclosed herein is that the steps are relatively unaffected by the overall size of the molecule of interest, such as the length of polymers. When the molecules are long synthetic oligos, gel electrophoresis and HPLC methods are unable to cleanly separate full-length products (e.g., X bases) from incomplete products (X-1 bases, X-2 bases, etc.). Thus, where purification of X-mers is difficult to achieve by conventional methods, the present disclosure provides a method for purifying only full-length molecules. Thus, the method is highly tolerant to oligo pools of varying quality.

Surprisingly, the method can be applied to complex pools to functionalize, in the same step, complex pools of molecules of interest. Conventional methods (such as gel electrophoresis or HPLC) are not practical for purifying mixtures en masse.

More Methods for Making Biotin-Oligonucleotides

Figure 6:
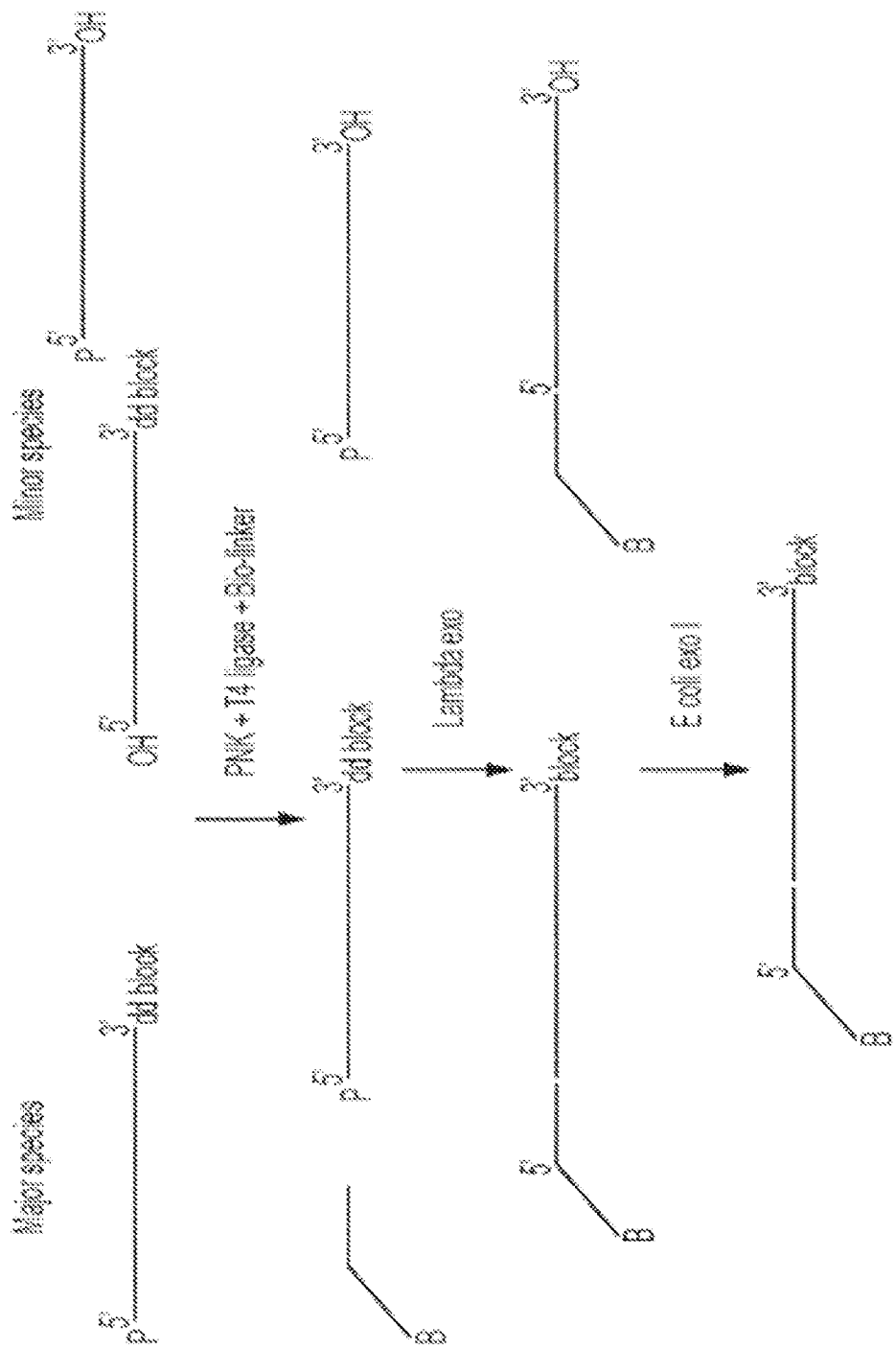
FIG. 6 depicts an alternate method for producing biotin-oligos.

Some embodiments of the methods provided herein include methods for making biotin-oligos entirely in liquid phase. Oligos are provided having a 5'-phosphate and a 3'-terminal block (3'-blocked oligo). The block can be a dideoxynucleotide or another phosphate (both of which can be added via commercially available phosphoramidites). An oligo having a functional group (5'-functional oligo) at the 5'terminus is also provided, such as an aldehyde-oligo, as long as the functional group is not a hydroxyl or phosphate. The 3'-blocked oligo and 5'-functional oligo are ligated to generate an oligo having 5'-functional group and the 3'-block. As an example, FIG. 6 depicts a 3'-blocked oligo (5'-phosphate-oligo-dideoxynucleotide-3') and a 5'-functional oligo (5'-biotin-oligo). The oligos are ligated with T4 ligase to form a full-length 5'-biotin-oligo-dideoxynucleotide-3' species that can be used in the other methods provided herein. If desired, the 3'-block can be removed by standard techniques.

As synthesis reactions to provide the 3'-blocked oligo ("major species") are not necessarily 100% efficient, the starting oligos may contain incomplete oligos that lack the 5'-phosphorylation or the 3'-dideoxynucleotide as undesired synthesis failures or "minor species". To remove these minor species from the reaction product, FIG. 6 further demonstrates that oligos with free 5'-hydroxyls can be phosphorylated with a kinase such as T4 polynucleotide kinase (PNK). The 5'-phosphorylated minor species can then be degraded by including an exonuclease in the reaction, such as lambda exonuclease, which preferentially digests 5'-phosphorylated oligos. To remove any residual, unreacted 5'-functional oligos, an exonuclease, such as E. coli exonuclease I can be further included in the reaction. Any remaining free nucleotides can be removed by simple ethanol precipitation, dialysis or size-exclusion chromatography. Thus, full-length biotin-oligos, unaffected by the exonucleases, can be produced by the method.

Use of Biotinylated Probes in Targeted Enrichment

When working with samples containing complex mixtures of molecules, such as genomic DNA, it can be useful to "pull out" target DNA sequences of particular interest, thereby selectively enriching the sample for the targeted sequences. In some methods of targeted enrichment, sequence-specific oligos are provided that are labeled with haptens, such as biotin. The oligos can be anchored (via streptavidin, for example) to a solid phase surface to serve as capture probes. When the capture probes anneal to the DNA sequences of interest, they can be pulled out from the complex mixture by means of the solid phase, for example easily handled paramagnetic beads.

For complete binding of biotinylated capture probes, it is advantageous to provide streptavidin beads in stoichiometric excess. As the complexity of the probe pool increases, however, the amount of streptavidin beads required for stoichiometric excess becomes prohibitive. This can be especially difficult when there are a large number of biotin-labeled probes that have not annealed to a target DNA, yet still compete for binding to streptavidin beads. Removal of excess biotin probe greatly reduces the amount of streptavidin beads required in the assay.

Figure 7:
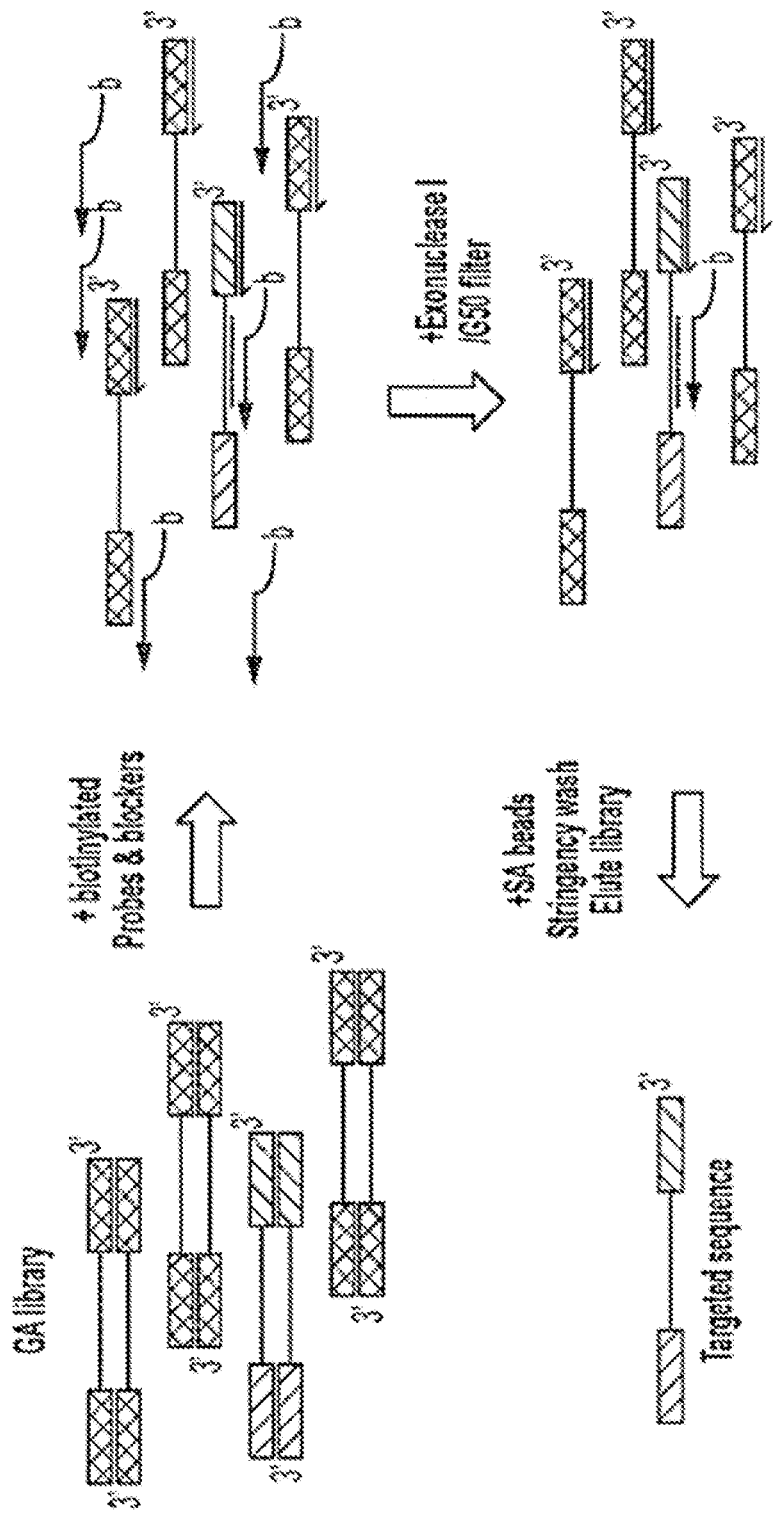
FIG. 7 depicts a method for using biotin-oligos for targeted enrichment

In one embodiment, excess probes can be removed by incubating the duplex probe-target mixture with exonuclease I, which digests single-stranded DNA from the 3' terminus (FIG. 7). The desired target:probe complexes can be protected by various methods provided herein. In another embodiment, phosphorothioate nucleotides can be added to the 3' terminus or body of the target library DNA. In yet another embodiment, blocking oligos can be annealed at the 3' end of the target DNA molecule to create 3' duplexes that are resistant to exonuclease I digestion. These blocking oligos are also useful to prevent target-target interactions leading to reduced enrichment. The method is highly scalable, as demonstrated in Example 5.

The following Examples provide illustrative embodiments and do not in any way limit the scope of the methods and compositions provided herein.

EXAMPLES

Example 1—Synthesis and Purification of His-Tagged Oligos

The following example describes the preparation of highly complex pools of 5'-aldehyde-labeled oligos. The 5'-aldehyde groups of the oligos were exchanged for His tags using reversible chemistry. The His-tags were useful for purifying the oligos on Ni-resins.

Synthesis of 5'-Aldehyde Oligos

Oligos with a 5'-aldehyde functional group were synthesized on an oligo synthesizer (Illumina. Inc., San Diego Calif.) at an average yield of 10 nmol per oligo. Individual oligos were normalized for concentration and combined in pools of about 42.000 complexity in 0.1×TE buffer. In other experiments, pools of 1.000 and 12,000 complexity were used.

Eight separate pools were prepared having varying ranges of % GC: Pool 1 (15-37% GC), Pool 2 (37-42%), Pool 3 (42-46%), Pool 4 (46-49%), Pool 5 (49-50%), Pool 6 (50-55%), Pool 7 (55-61%), Pool 8 (61-88%). For the 42K pools, 300 ml was precipitated with cold ethanol/sodium acetate. The pellet was washed once with 25 ml cold 70% ethanol and dried overnight in a vacuum oven at room temperature. The pellet was redissolved in 150 ml of 1 M citrate buffer, pH 6.0.

For more detailed mass spectroscopy analysis of the process, a single reference oligo (about 95 bp) was also obtained, having a 5'-aldehyde functional group (TriLink Biotechnologies, San Diego Calif.). The 8 pools of oligos and the single reference oligo were processed in a similar manner as described below.

Preparation of 5' his-Labeled Oligos by Exchange

The 5'-aldehyde oligos were quantified by optical absorbance spectroscopy on a NanoDrop UV-Vis instrument (Thermo Fisher Scientific) to be a total of 30 μma Next, 10M urea was added, bringing the concentration of the oligo to 1 mM. A solution of 0.66 g HyNic/PEG2/Hexa-His reagent (Solulink) in 1 ml 1M citrate buffer. pH 6.0 was prepared and added to the oligo mixture, resulting in a 20:1 molar excess of His-reagent:oligo. Next, 2.1 g of neat aniline was added for a final aniline concentration of 100 mM. The exchange mixture incubated on a rotisserie apparatus for 1 hour at room temperature. The oligos were precipitated with cold ethanol/sodium acetate, washed three times with cold 70% ethanol, and then vacuum-dried at room temperature for 4 hours. The pellets were redissolved in pre-warmed HPLC-grade water, yielding unpurified 5'-His-labeled oligos.

Purification of 5'-his-Labeled Oligos

Nickel chromatography resin beads having up to 60 mg/ml protein-binding capacity (His60 Ni Superflow Resin, Clontech) was prepared as 200 ml of pre-homogenized slurry in two separate 225 ml centrifuge tubes, and centrifuged at 1200 rfu for 5 min (Eppendorf 5810 benchtop centrifuge). The supernatant was removed by aspiration and discarded: the resin was washed with 100 ml 8M urea in 5×PBS buffer, pH 7.4. The washing was repeated three times to equilibrate the resin.

After equilibration of the Ni resin slurry, a 25 ml aliquot of the unpurified 5'-His-labeled oligo product was added to each centrifuge tube. An additional 75 ml of 5×PBS buffer containing 8M urea was added to each tube, and the tube was placed on the rotisserie at room temperature for at least 16 hours. After incubation, the tubes were centrifuged at 1200 rfu for 5 min at room temperature. The supernatant was removed by aspiration and discarded. The Ni resin was transferred to a plastic Büchner vacuum filter flask and washed with 500 ml Wash Buffer: 1×PBS containing 20 mM imidazole. Next, the resin was washed with 20 ml of 0.01N NaOH and subsequently washed with Wash Buffer. The washed Ni resin was divided into two aliquots and transferred to fresh 225 ml centrifuge tubes.

To each tube was added 100 ml Elution Buffer: 500 mM imidazole and 1×PBS buffer (optionally with 10 mM DTT). The tubes were placed on the rotisserie for 5 min and centrifuged for 5 min at 1200 rfu. The liquid was aspirated and collected. The Ni resin was then transferred to a Büchner vacuum filter flask and washed, in parts, with 500 ml of 500 mM imidazole solution and 1×PBS buffer. The collected washings were concentrated to about 15 ml using a Centricon 70 (10 kDa MWCO) centrifugal dialysis assembly (Millipore PN UFC701008). The solution was washed with 4×50 ml HPLC-grade water, concentrating the His-tagged oligo product after each wash with the Centricon centrifugal dialysis assembly and concentrated to about 20 ml. A 10 µl aliquot of the concentrated solution was quantified using the Nanodrop instrument. Of the solution obtained from the single reference oligo, a 20 µl aliquot of a 10 µM solution was analyzed by LC-MS, and another 10 µl aliquot was analyzed by FPLC.

Preparation of 5' Biotin-Labeled Oligos by Exchange

The His-tagged oligo product was transferred to a new 225 ml centrifuge tube. Then, 150 ml of 1M citrate buffer at pH 6.0 and 150 ml of 10M urea solution were added. A molar excess (e.g. 5- to 10-fold) of biotin-oxo amine (biotin-aldoxime, Aldehyde Reactive Probe, Dojindo Molecular Technologies, PN A305-10) was added relative to the amount of oligo, e.g., for 30 µmol of total oligo, 150 µmol to 300 µmol of the biotin oxo-amine was added. Alternately, biotin-HyNic (Solulink) or biotin-hydrazide was used (Thermo Scientific. Pierce research products), for example at 5- to 15-fold molar excess. Subsequently, 2.7 g of aniline was added, and the exchange mixture was incubated on a rotisserie at room temperature for 4 hours. The oligos were then precipitated using cold ethanol/sodium acetate, the pellet washed with 3× with cold 70% ethanol, and the pellet was dried in a vacuum oven overnight at room temperature. The pellet was redissolved in pre-warmed 50 ml of HPLC-grade water.

A 50 ml solution of the biotinylated oligos were contacted with the Ni resin as described above, but the washings were collected and retained. The washings were concentrated using a Centricon 70 centrifugal dialysis apparatus as described above, and washed 4×50 ml with HPLC-grade water down to a final concentration of about 25 ml in HPLC-grade water. A 10 µl aliquot of the final purified solution was quantified with optical absorbance spectroscopy on a Nanodrop instrument, and for LC-MS and FPLC analyses. The final yield was 7.5 µma for a total process yield of 25%. The His- and biotin-oligos can be stored and were stable for at least 6 months.

Example 2—Analysis of his-Oligo Pools by FPLC

FPLC analysis was performed with an Akta Explorer FPLC system (GE Healthcare) fitted with a nickel-resin cartridge (HisPur Ni-NTA Chromatography Cartridge. Pierce Biotechnology), using a method similar to that described by the column vendor for FPLC analysis of His-labeled molecules. The signal of the oligos was monitored at 280 nm. The samples were prepared as 50 µL volume in water at 20 µM concentration. The flow rate was set at 0.2 ml/min. The binary solvent profile was 100% Buffer A until after the non-Histidine-containing oligos were eluted (approx. 25 min), then 100% Buffer B to elute off the His-oligos. Buffer A consisted of 50 mM Phosphate. pH 7.4, 20 mM imidazole; 300 mM NaCl. Buffer B consisted of 50 mM Phosphate, pH 7.4, 300 mM imidazole, 300 mM NaCl.

Figure 8:
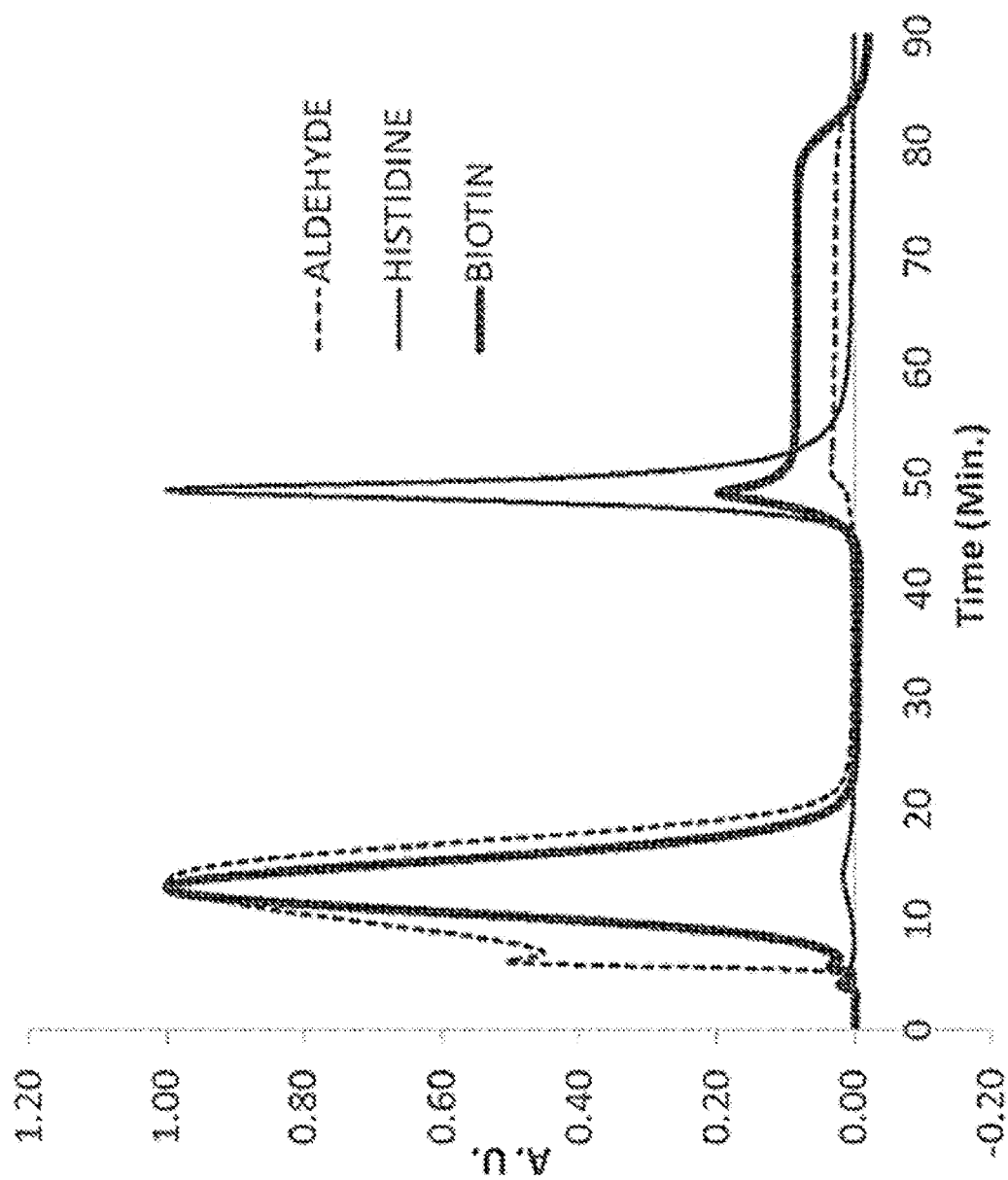
FIG. 8 depicts overlaid FPLC traces of oligo pool 2 (42 k complexity) at different stages of functionalization. Dotted trace A: starting pool of 5'-aldehyde-oligos. Thin trace: pool after exchanging 5'-aldehyde with His. Thick trace: pool after exchanging 5'-His with biotin.

The chemical transformation, purity, and yield of the pools were established by capturing the FPLC trace signal (FIG. 8). The reported yields and purities were validated by using pure His-oligos as input material. Overall, a purity was obtained of 97-99% (pool 1-6), 95% (pool 7), 90% (pool 8).

Figure 9:
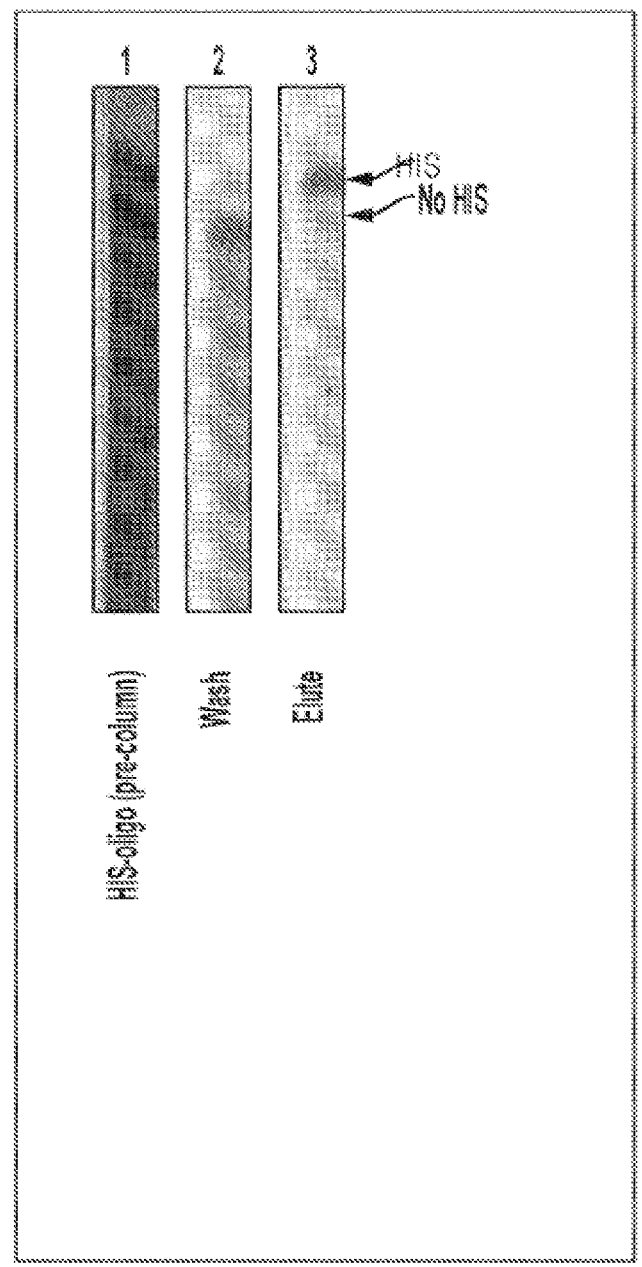
FIG. 9 depicts a gel electrophoretic analysis of an oligo pool (42 k complexity) at different stages of purification using a nickel IMAC resin. Lane 1: pool of His-oligos prior to purification on a Ni-column. Lane 2: wash fraction from Ni-column, showing unbound oligos lacking a His tag. Lane 3: eluate collected from Ni-column, showing purified His-oligos.

Analysis by gel electrophoresis demonstrated that after Ni-column purification, impurities such as truncated oligos were efficiently removed. Moreover, a single band for the His-tagged product was observed (FIG. 9, lane 3). A minor reduction in purity was observed going from low to high percent GC pools. For example, pool 1 had a purity of 95%, while pool 8 had a purity of 85% using FPLC analysis.

Example 3—Analysis of Reference Oligo by LC-MS

Figure 10:
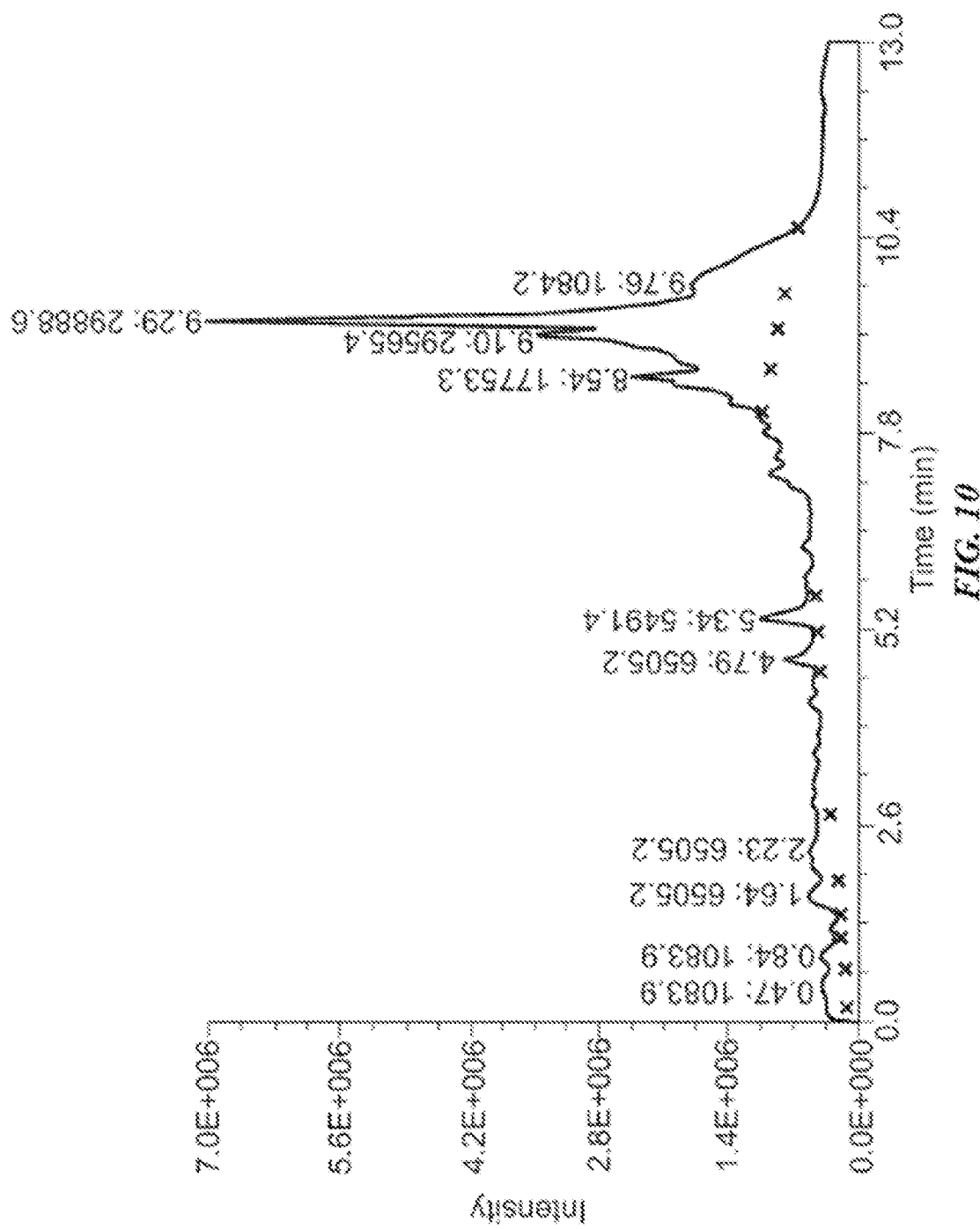
FIG. 10 shows a liquid chromatography (LC) elution profile of a reference 5'-aldehyde-oligo (95 mer).
Figure 11:
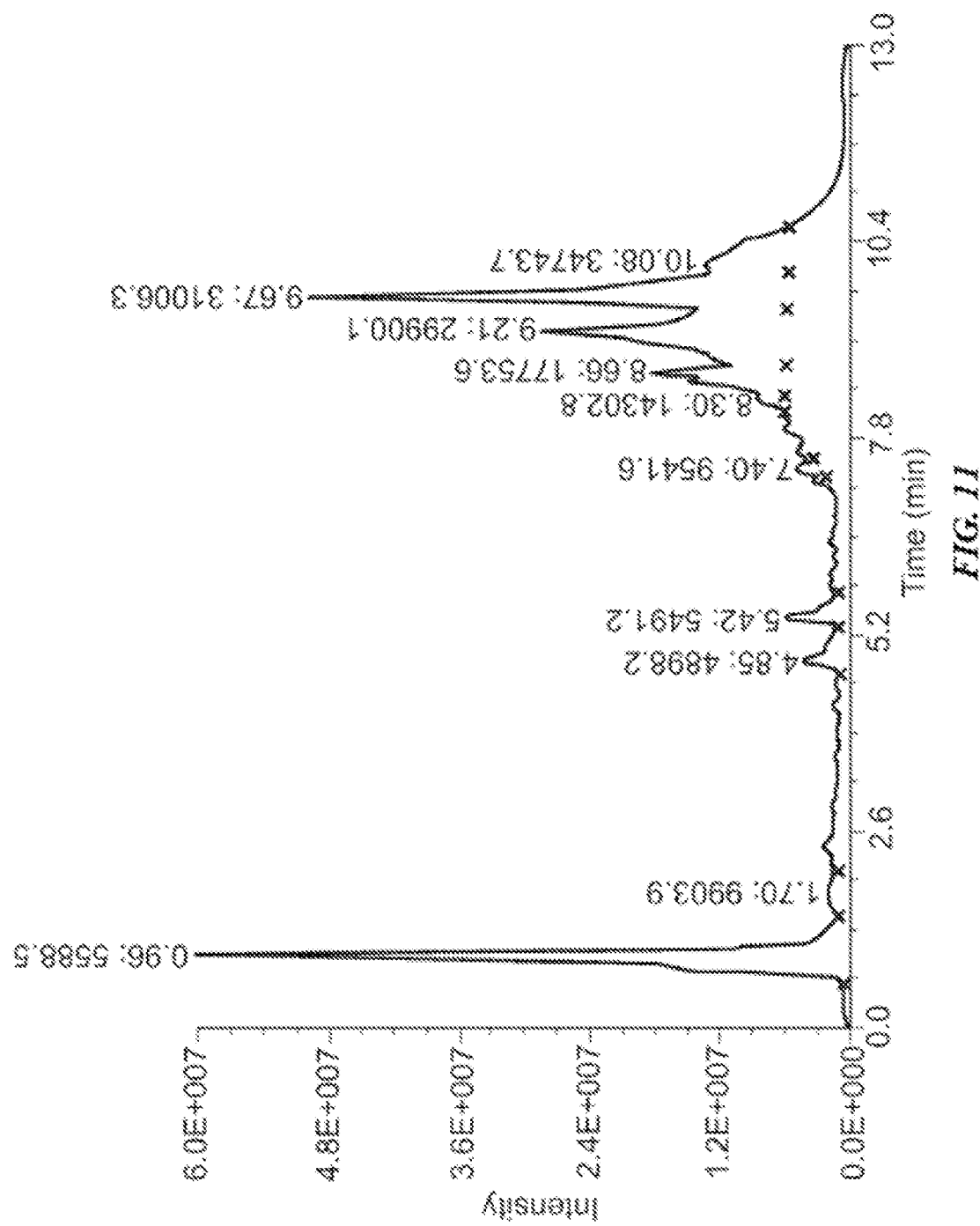
FIG. 11 shows the LC elution profile of the oligo after exchange of the 5'-aldehyde for His, prior to purification on a Ni-column.
Figure 12:
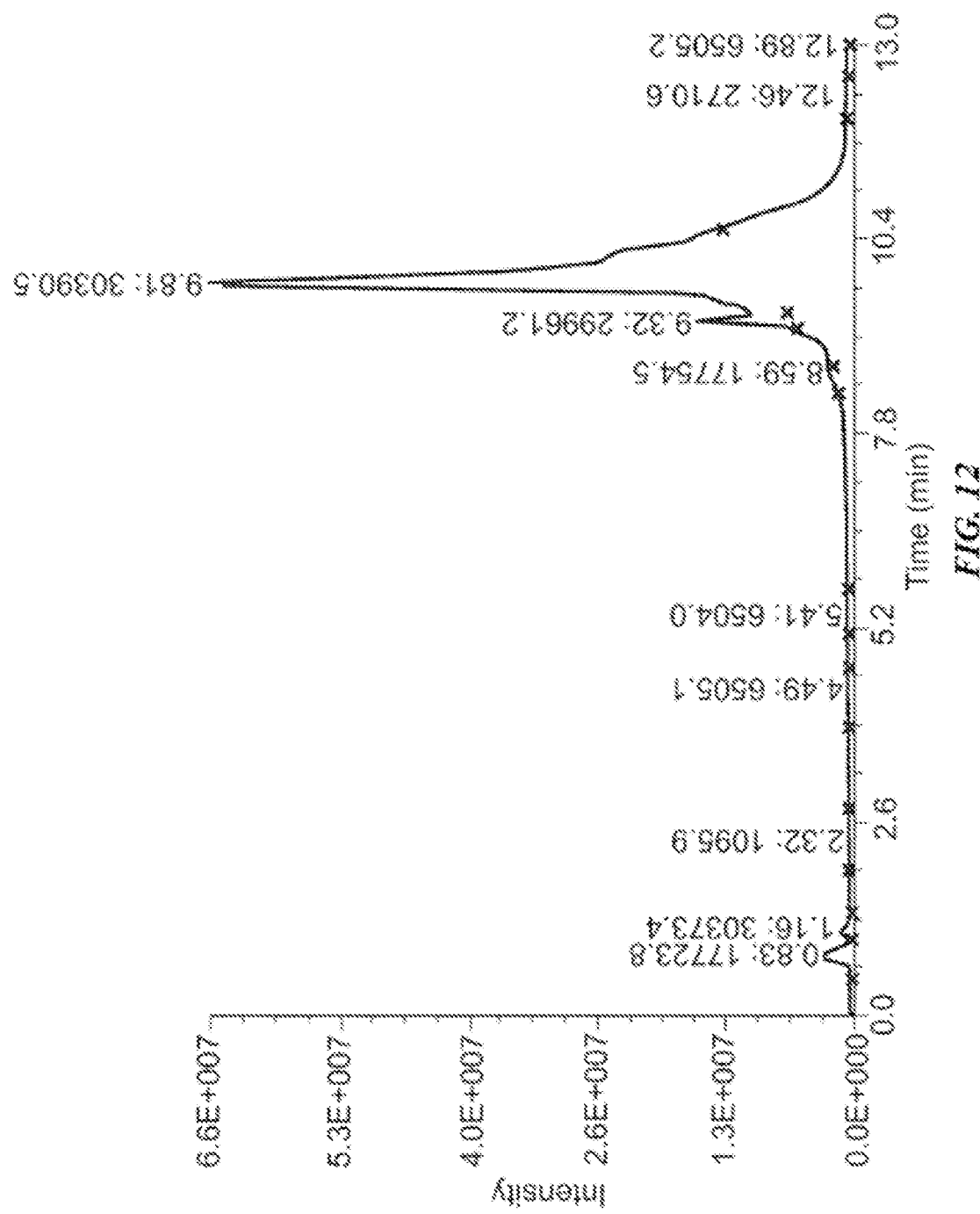
FIG. 12 shows the LC elution profile of the oligos after purification on a Ni-column and exchange of the 5'-His by biotin. The major peak of the LC elution (biotin-oligo, retention time of 9.81 min) was further analyzed by mass spectroscopy (MS), as shown in FIG. 13.
Figure 13:
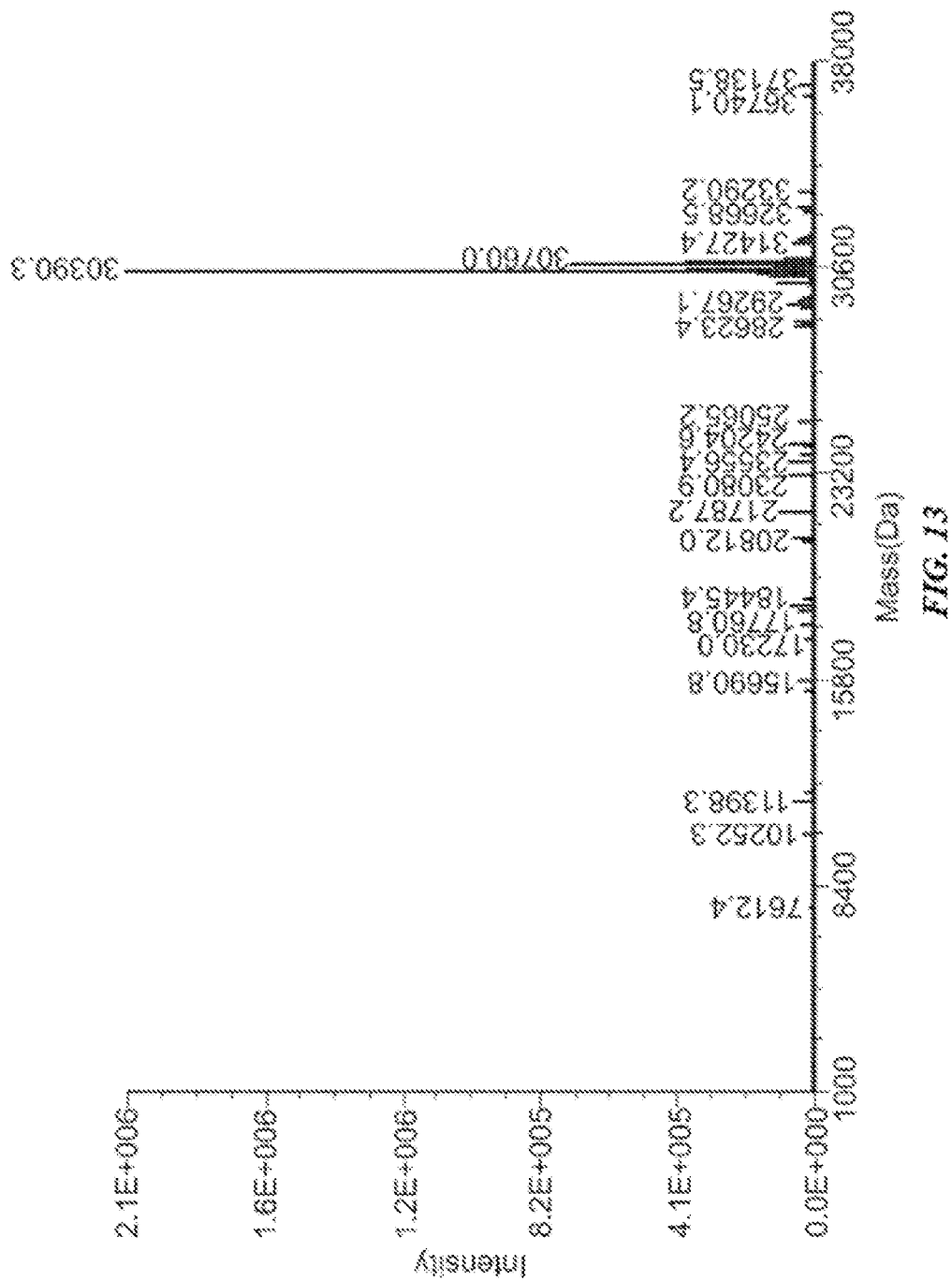
FIG. 13 depicts the MS ion fragmentation pattern and relative ion abundance of the major peak of FIG. 12, demonstrating the relative purity of the biotin-oligo product.

Mass spectrometry was performed on the single reference oligo by liquid chromatography-mass spectrometry (LC-MS) (Novatia, LLC). The oligo was found to incorporate the His tag at the aldehyde site after the first reaction, and then exchange the biotin functionality for the His tag after the second reaction. Furthermore, the LC-MS analysis of the purified oligo found no starting material, no His-tag intermediate products, and no synthesis truncation anomalies of the final biotinylated product. FIG. 10 shows an LC-MS trace of the 95 bp oligo with a 5'-aldehyde modifier, 9.29 min. peak corresponds to the 5'-aldehyde oligonucleotide (Expected MW: 29888. Found: 29888). FIG. 11 shows an LC-MS trace of non-purified 95 bp oligo with the 5'-hexa-His modifier, 9.67 min peak corresponds to the 5'-hexa-His oligonucleotide (Expected MW: 31006, Found: 31006). FIG. 12 shows an LC-MS trace of the processed 95 bp oligo with the 5'-biotin functionality, 9.81 min peak corresponds to the 5'-Biotin oligonucleotide (Expected MW: 30390. Found: 30390). FIG. 13 shows an MS expansion of the 9.81 min retention time peak, demonstrating the high purity of the biotinylated product. Expected MW: 30390, Found: 30390).

Example 4—Improvement of Binding and Elution with Urea

Several steps were identified to further improve the binding and elution of the target oligos. Improvements included the addition of urea during the Ni-column binding step; addition of a slurry of His-oligonucleotide to Ni-Resin with an increased binding time of up to 4 hours; addition of urea in the exchange reaction; and the addition of 0.01 N NaOH wash. Each of these steps was found to either improve yield or increase purity. For example, the addition of urea in the exchange reaction improved yields by 20%-70%. An additional advantage of urea is the prevention of undesirable cross-hybridization between intermediate oligo products, such as two His-oligos.

The reported yields were validated using pure His-oligo-nucleotides as input material. The purity and labeling degree was established by capturing the FPLC trace signal. Additional confirmation that the final purified biotin-oligonucleotides were biotin labeled was obtained by performing a streptavidin-shift assay with the biotin-modified oligonucleotides, then analyzing by gel electrophoresis. Measuring the reduction in gel migration with excess streptavidin (versus no streptavidin) showed that all products shift completely upon addition of streptavidin. The results are summarized in Table 1.

TABLE 1

| Pool/fraction | (%) |
| --- | --- |
| Aldehyde-labeled oligonucleotides have "non-oligo" with OD$_{260}$ absorbance: | ~50% |
| Aldehyde-oligos: | ~60% |
| Yield for His-to-biotin exchange: | >90% |
| Streptavidin gel-shift assay confirms biotinylated: | >95% |
| Purity of pool 1-6: | 97-99% |
| Purity of pool 7: | 95% |
| Purity of pool 8: | 90% |
| Overall yield per pool: | ~25% |

The above method was performed on a single 95 bp oligonucleotide with an aldehyde group at the 5' end. At particular stages in the method, the oligonucleotide was analyzed using liquid chromatography-mass spectrometry (LC-MS; Novatia LLC). The oligos were found to incorporate the His-tag at the aldehyde site after the first reaction, and then exchange the biotin functionality for the His-tag after the second reaction. Furthermore, the LC-MS showed no starting material, no His-tag intermediate products, and no synthesis truncation anomalies. The results are depicted in FIG. 10.

The results showed that crude oligonucleotide loading as high as 150 μmol per column were readily processed, resulting in product recovery of greater than 50% and purity of greater than 95%.

Example 5—Use of Biotin-Oligos for Targeted Enrichment of Samples

This example demonstrates a scalable, targeted enrichment method using biotin-oligos and exonuclease I. An enrichment pool of about 2500 different biotinylated oligos was prepared. A separate pool was prepared with exogenous biotinylated oligo non-complementary to any of the target library elements. Excess biotinylated oligos were spiked into a 2.5 k (2500) complexity enrichment oligo pool at varying levels to mimic 10 k, 60 k, 100 k, 200 k, and 400 k total oligo complexity.

Figure 14A:
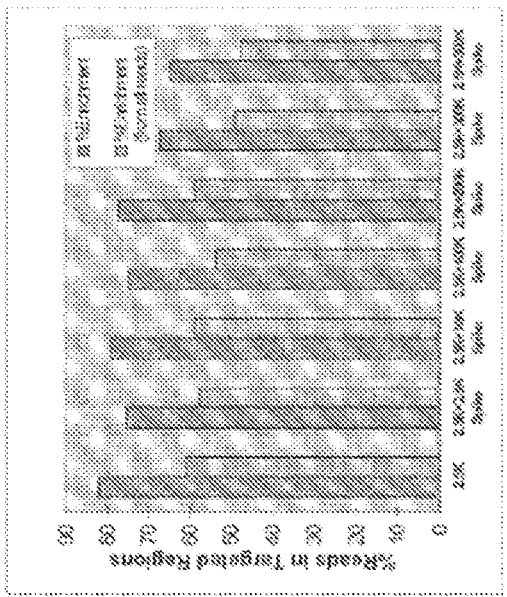
FIGS. 14A-D show a series of graphs, depicting results discussed in Example 5.
Figure 14B:
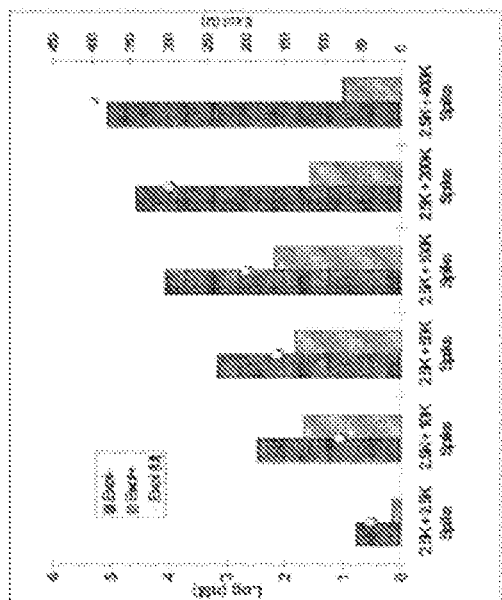
Figure 14D:
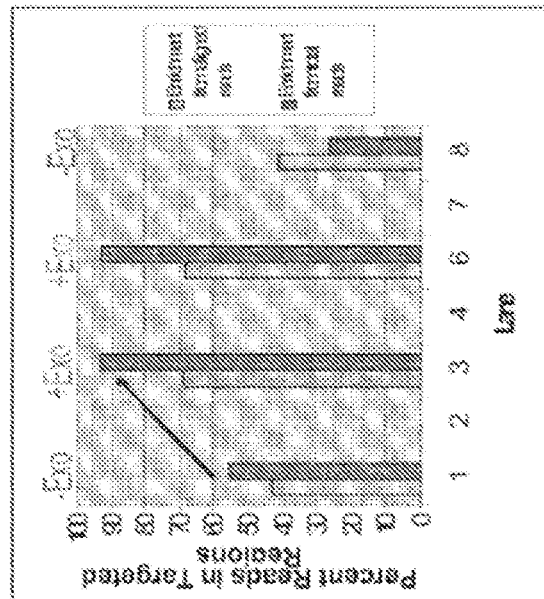
Figure 14C:
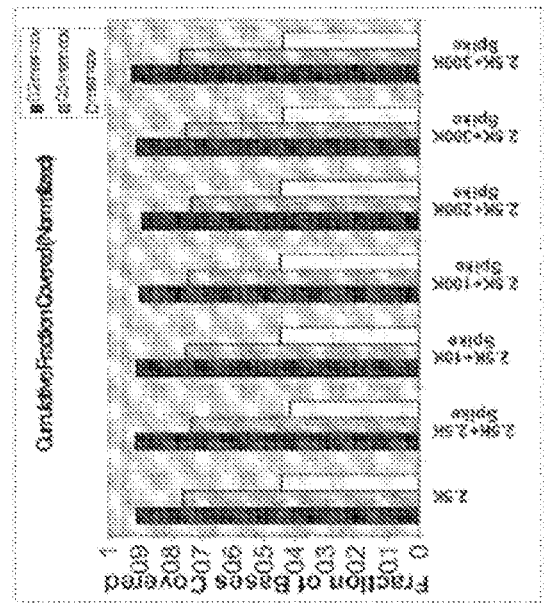

FIG. 14A is a bar graph showing the amount of excess biotinylated oligo remaining in supernatant after streptavidin pull-down. The excess oligo limited the effective capture of biotinylated probe-target duplexes. Without ExoI treatment, a large excess of biotinylated oligo remained. With ExoI treatment (ExoI+), however, the amount of excess biotinylated oligo was reduced by up to 100,000-fold (5 logs). FIG. 14B and FIG. 14C demonstrate that a large spike of biotinylated oligos did not adversely affect the enrichment or coverage when ExoI was used in the assay. This suggests the enrichment assay can be scaled up to 300,000 loci (human exome scale). FIG. 14D shows enrichment using a biotinylated oligo pool of 55 k complexity, with and without ExoI in the assay. The inclusion of ExoI greatly improved the enrichment efficiency.

The headings and subheadings used herein are only for reading convenience and are not intended to define or limit the scope of the present disclosure. The present disclosure describes several compositions and methods that are susceptible to modifications in the methods and materials, as well as alterations in the fabrication methods and equipment. Such modifications will become apparent to those skilled in the art from a consideration of this disclosure or practice of the embodiments disclosed herein. Consequently, it is not intended that this disclosure be limited to the specific embodiments disclosed herein, but that it cover all modifications and alternatives coming within the true scope and spirit of the invention.

All references cited herein including, but not limited to, published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The invention claimed is:

1. A method of making functionalized-oligonucleotides, comprising:
    providing at least two sets of oligonucleotides, a first set of oligonucleotides comprising a 5'-phosphate and a 3'-terminal block, and a second set of oligonucleotides comprising a 5'-functional group, wherein the 5'-functional group is an aldehyde group or comprises a biotin moiety;
    ligating an oligonucleotide from the first set of oligonucleotides with an oligonucleotide from the second set of oligonucleotides to form functionalized-oligonucleotides; and
    removing non functionalized-oligonucleotides by adding:
    (1) an exonuclease that digests unreacted oligonucleotides from the first set of oligonucleotides by preferentially digesting 5'-phosphorylated oligonucleotides;
    (2) an exonuclease that digests unreacted oligonucleotides from the second set of oligonucleotides, or
    (3) both (1) and (2).

2. The method of claim 1, wherein the 3'-terminal block is a dideoxynucleotide.

3. The method of claim 1, wherein the oligonucleotide from the first set of oligonucleotides is ligated with an oligonucleotide from the second set of oligonucleotides by using T4 ligase.

4. The method of claim 1, wherein the exonuclease of (1) is a lambda exonuclease.

5. The method of claim 1, wherein the exonuclease of (2) is *E. coli* exonuclease I.

6. The method of claim 1, wherein any non-functionalized oligonucleotides that comprise a 5'-OH group can be phosphorylated with T4 polynucleotide kinase prior to adding the exonuclease of (1) and/or the exonuclease of (2).

7. The method of claim 1, wherein the 5'-functional group of the second set of oligonucleotides comprises a biotin moiety.

8. The method of claim 1, wherein the 5'-functional group of the second set of oligonucleotides comprises an aldehyde group.

9. The method of claim 8, the method further comprising:
    reacting the aldehyde group of the functionalized oligonucleotide with a bifunctional linking reagent comprising a hydrazine or amine moiety under conditions to form an imine bond between the functionalized-oligonucleotide and the bifunctional linking reagent, wherein the bifunctional linking reagent further comprises a functional tag selected from the group consisting of polyhistidine, biotin, and glutathione-S-transferase, and contacting oligonucleotides comprising the first functional tag with a first binding partner selected from the group consisting of nickel, avidin, streptavidin, and glutathione and separating the oligonucleotides bound to the first binding partner from the other reaction components in order to isolate oligonucleotides comprising the first functional tag.

10. The method of claim 9, wherein the bifunctional linking reagent comprises a 6-hydrazinonicotinate acetone hydrazone moiety or derivative thereof.

11. The method of claim 9, the method further comprising:

performing an exchange reaction by exchanging the first functional tag of the oligonucleotides with a second functional tag by breaking the imine bond formed between the functionalized oligonucleotide and the bifunctional linking ligand and forming a new imine bond with a second functional tag selected from the group consisting of polyhistidine, biotin, and glutathione-S-transferase; and contacting oligonucleotides comprising the second functional tag with a seconding binding partner selected from the group consisting of nickel, avidin, streptavidin, and glutathione and separating the oligonucleotides bound to the second binding partner from the other reaction components in order to isolate oligonucleotides comprising the second functional tag.

12. The method of claim 11, wherein the first binding partner and the second binding partner are the same.

13. The method of claim 11, wherein the first functional tag and the second functional tab are different.

14. The method of claim 13, wherein the first functional tag is polyhistidine, and the second functional tag is biotin.

* * * * *